United States Patent [19]

Bergeron et al.

[11] Patent Number: 5,691,306

[45] Date of Patent: Nov. 25, 1997

[54] METHODS OF DETECTION AND TREATMENT OF PROTEIN TRAFFICKING DISORDERS AND INCREASING SECRETORY PROTEIN PRODUCTION

[75] Inventors: John J. M. Bergeron, Pointe-Claire; David Y. Thomas, Montreal West, both of Canada; Ikuo Wada, Sapporo, Japan

[73] Assignee: National Research Council of Canada, Ottawa, Canada

[21] Appl. No.: 296,362

[22] Filed: Aug. 25, 1994

Related U.S. Application Data

[63] Continuation-in-part of Ser. No. 112,395, Aug. 26, 1993, abandoned.

[51] Int. Cl.⁶ .............................. A61K 38/00; C07K 7/00
[52] U.S. Cl. ........................................ 514/11; 435/70.1
[58] Field of Search ............................ 514/11; 435/70.1

[56] References Cited

FOREIGN PATENT DOCUMENTS

WO 93/13788  7/1993  WIPO ....................... A61K 37/00
WO93/13768  7/1993  WIPO ....................... A61K 31/40

OTHER PUBLICATIONS

Ou et al., "Conformational Changes Induced in the Endoplasmic Reticulum Luminal Domain of Calnexin by Mg–ATP in $Ca^{2+}$*" J. Biol. Chem., vol. 2(30) pp. 18051–18059 (1995).

Volpe et al., "The endoplasmic reticulum–sarcoplasmic reticulum connection: Distribution of endoplasmic reticulum markers in the sarcoplasmic reticulum of skeletal muscle fibers," Proc. Natl. Acad. Sci. (USA) 89:6142–6146, 1992.

Pelham et al., "Toxin entry: how reversible is the secretory pathway?," Trends in Cell Biology 2: 183–185, 1992.

Bergeron et al., "Calnexin: a membrane–bound chaperone of the endoplasmic reticulum," Trends in Biochem. Sci. 19(3): 124–128, 1994.

Ou et al., "Association of folding intermediates of glycoproteins with calnexin during protein maturation," Nature 364: 771–776, 1993.

Pind et al., "Interaction Of CFTR With The Chaperone P88 (Calnexin) During Biosynthesis In The ER," FASEB 7(7): A1245, 1993.

David et al., "Interaction with Newly Synthesized and Retained Proteins in the Endoplasmic Reticulum Suggests a Chaperone Function for Human Integral Membrane Protein IP90 (Calnexin)," Journal of Biological Chemistry 268(13): 9585–9592, 1993.

Wada et al., "SSRα and Associated Calnexin Are Major Calcium Binding Proteins of the Endoplasmic Reticulum Membrane," Journal of Biological Chemistry 266: 19599–19610, 1991.

Ahluwalia et al., "the p88 Molecular Chaperone Is Identical to the Endoplasmic Reticulum Membrane Protein, Calnexin," Journal of Biological Chemistry 267(15): 10914–10918, 1992.

Hochstenbach et al., "Endoplasmic reticulum resident protein of 90 kilodaltons associates with the T–and B–cell antigen receptors and major histocompatibility complex antigens during their assembly," Proc. Natl. Acad. Sci. (USA) 89: 4734–4738, 1992.

Baksh and Michalak, "Expression of Calreticulin in Escherichia coli and Identification of Its $Ca^{2+}$ Binding Domains," Journal of Biological Chemistry 266(32): 21458–21465, 1991.

Degen and Williams, "Participation of a Novel 88–kD Protein in the Biogenesis of Murine Class I Histocompatibility Molecules," Journal of Cell Biology 112(6): 1099–1115, 1991.

Görlich et al., "The Signal Sequence Receptor Has a Second Subunit and Is Part of a Translocation Complex in the Endoplasmic Reticulum as Probed by Bifunctional Reagents," Journal of Cell Biology 111(No.6, Pt.1):2283–2294,1990.

DeVirgilio et al., "CNE1, a Saccharomyces cerevisiae Homologue of the Genes Encoding Mammalian Calnexin and Calreticulin," Yeast 9: 185–188, 1993.

Hawn et al., "Molecular Cloning and Expression and SmIrV1, a Schistosoma mansoni Antigen with Similarity to Calnexin, Calreticulin, and OvRa11," Journal of Biological Chemistry 268(11):7692–7698, 1993.

Huang et al., "Primary Structure and Characterization of an Arabidopsis thaliana Calnexin–like Protein," Journal of Biological Chemistry 268(9):6560–6566, 1993.

Gilchrist and Pierce, "Identification and Purification of a Calcium–binding Protein in Hepatic Nuclear Membranes," Journal of Biological Chemistry 268(6): 4291–4299, 1993.

Cala et al., "Purification of a 90–kDa Protein (Band VII) from Cardiac Sarccoplasmic Reticulum. Identification as calnexin and localization of casein kinase II phosphorylation sites," Journal of Biological Chemistry 268(4): 2969–2975, 1993.

Villa et al., "The Endoplasmic Reticulum Of Purkinje Neuron Body And Dendrites: Molecular Identity And Specializations For $Ca^{2+}$ Transport," Neuroscience 49(2): 467–477, 1992.

Ou et al., "Casein Kinase II Phosphorylation of Signal Sequence Receptor α and the Associated Membrane Chaperone Calnexin," Journal of Biological Chemistry 267(33): 23789–23796, 1992.

Beckmann et al., "Interaction of Hsp 70 with Newly Synthesized Proteins: Implications for Protein Folding and Assembly," Science 248: 850–854, 1990.

(List continued on next page.)

Primary Examiner—Howard E. Schain
Assistant Examiner—P. L. Touzeau
Attorney, Agent, or Firm—Seed and Berry LLP

[57] ABSTRACT

The present invention provides compositions and methods for increasing secretory protein production. In another aspect, the present invention provides compositions for use in methods of treating and diagnosing protein trafficking disorders. These methods generally involve the alteration of calnexin activity to increase protein secretion or retention.

8 Claims, 11 Drawing Sheets

OTHER PUBLICATIONS

Booth and Koch, "Perturbation of Cellular Calcium Induces Secretion of Luminal ER Proteins," *Cell* 59: 729–737, 1989.

Bradford, M., "A Rapid and Sensitive Method for the Quantitation of Microgram Quantities of Protein Utilizing the Principle of Protein–Dye Binding," *Analytical Biochemistry* 72: 248–254, 1976.

Galvin et al., "The major histocompatibility complex class I antigen–binding protein p88 is the product of the calnexin gene," *Proc. Natl. Acad. Sci.(USA)* 89: 8452–8456, 1992.

Gething and Sambrook, "Protein folding in the cell," *Nature* 355: 33–45, 1992.

Laemmli, U., "Cleavage of Structural Proteins during the Assembly of the Head of Bacteriophage T4," *Nature* 227: 680–685, 1970.

Wiedmann et al., "A signal sequence receptor in the endoplasmic reticulum membrane," *Nature* 328: 830–833, 1987.

Walter and Blobel, "Preparation of Microsomal Membranes for Cotranslational Protein Translocation," *Methods in Enzymology* 96: 84–93, 1983.

Louvard et al., "Antibodies in the Golgi Complex and the Rough Endoplasmic Reticulum," *Journal of Cell Biology* 92: 92–107, 1982.

Liu et al., "Purification And Characterization Of The Apically Secreted 80 KDa Glycoprotein From Madin–Darby Canine Kidney (MDCK) Cells," *Biochemistry International* 25(1): 109–121, 1991.

Migliaccio et al., "The Signal Sequence Receptor, Unlike the Signal Recognition Particle Receptor, Is Not Essential for Protein Translocation," *Journal of Cell Biology* 117(1): 15–25 1992.

Nicchitta et al., "Biochemical Fractionation and Assembly of the Membrane Components That Mediate Nascent Chain Targeting and Translocation," *Cell* 65: 587–598, 1991.

Prehn et al., "Structure and biosynthesis of the signal–sequence receptor," *European Journal of Biochemistry* 188: 439–445, 1990.

Rindress et al., "Organelle–specific Phosphorylation. Identification of unique membrane phosphoproteins of the endoplasmic reticulum and endosomal apparatus," *Journal of Biological Chemistry* 268(7): 5139–5147, 1993.

Suzuki et al., "Regulating the Retention of T–Cell Receptor α Chain Variants within the Endoplasmic Reticulum: $Ca^{2+}$–dependent Association with BiP," *Journal of Cell Biology* 114(2): 189–205, 1991.

Valetti et al., "Russels Bodies: A General Response of Secretory Cells to Synthesis of a Mutant Immunoglobulin Which Can Neither Exit from, Nor Be Degraded in, the Endoplasmic Reticulum," *Journal of Cell Biology* 115(4): 983–994, 1991.

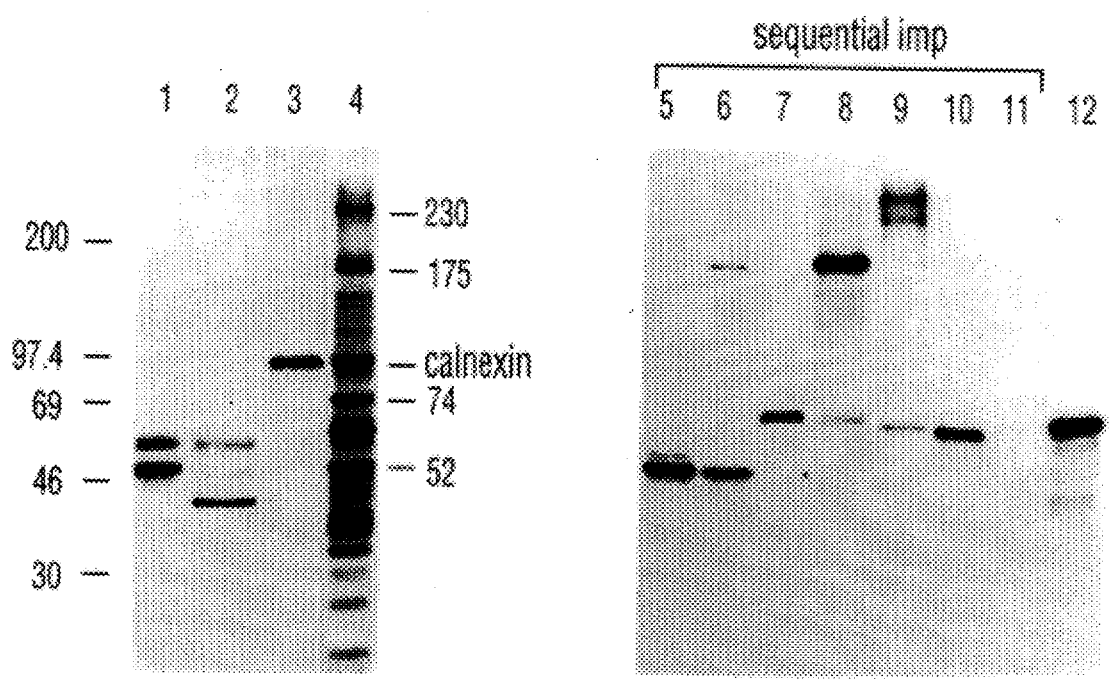
FIG. 1a
FIG. 1c
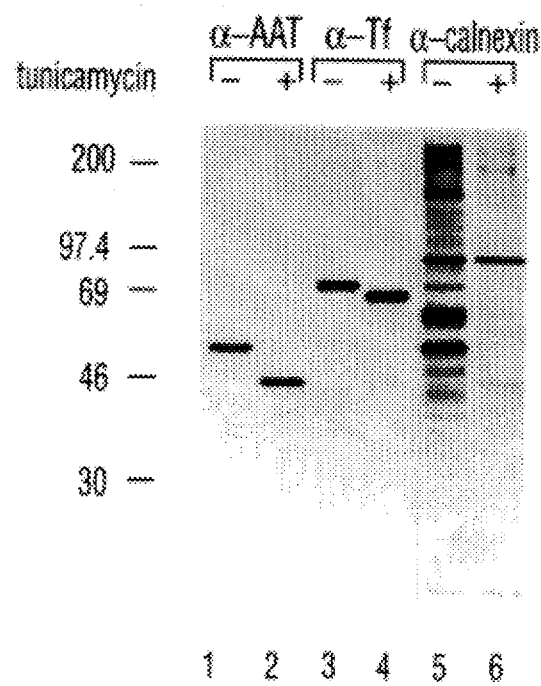
FIG. 1b

```
5'CGCGGCTCGTGACGGTCGGGCAGCCTCCGCTGCTGTCTCCACTGCAGCGCGGGCCGGGCG           60
TGCGGGCGGGTGGAGGCGCGGGCCGCGCACGACTCGAGATC ATG GAA GGG AAA TGG CTG        119
                                          M   E   G   K   W   L
                                         -20
```

```
CTG TGT ATG TTA CTG GTC CTT GGA ACT ACT ATT GTT CAG GCT CAT GAA GGA     170
 L   C   M   L   L   V   L   G   T   T   I   V   Q   A   H   E   G
                -10                                      -1   1

CAT GAT GAT GAT ATG ATT GAT ATT GAG GAC GAC CTC GAT GAT GTT ATT GAA     221
 H   D   D   D   M   I   D   I   E   D   D   L   D   D   V   I   E
                         10                                      20

GAG GTA GAA GAC TCC AAA TCA AAA CCA GAT ACC AGC GCT CCT ACA TCT CCA     272
 E   V   E   D   S   K   S   K   P   D   T   S   A   P   T   S   P
                                     30

AAG GTC ACC TAT AAA GCT CCA GTT CCT TCC GGG GAA GTG TAT TTT GCT GAT     323
 K   V   T   Y   K   A   P   V   P   S   G   E   V   Y   F   A   D
             40                                  50

TCC TTT GAC AGA GGA ACT CTG TCA GGG TGG ATT TTA TCA AAA GCC AAG AAG     374
 S   F   D   R   G   T   L   S   G   W   I   L   S   K   A   K   K
                         60                                      70

GAT GAC ACT GAT GAT GAA ATT GCC AAA TAT GAC GGA AAG TGG GAG GTA GAT     425
 D   D   T   D   D   E   I   A   K   Y   D   G   K   W   E   V   D
                                 80

GAA ATG AAG GAA ACA AAG CTC CCA GGT GAT AAA GGG CTT GTG TTG ATG TCT     476
 E   M   K   E   T   K   L   P   G   D   K   G   L   V   L   M   S
     90                                          100

CGG GCC AAG CAT CAT GCC ATC TCT GCA AAA CTC AAC AAG CCC TTC CTG TTT     527
 R   A   K   H   H   A   I   S   A   K   L   N   K   P   F   L   F
                 110                                      120

GAT ACC AAG CCT CTC ATT GTT CAG TAT GAG GTT AAT TTC CAA AAT GGA ATA     578
 D   T   K   P   L   I   V   Q   Y   E   V   N   F   Q   N   G   I
                             130

GAA TGT GGT GGT GCC TAT GTG AAA CTG CTT TCC AAA ACC CCC GAA CTC AAC     629
 E   C   G   G   A   Y   V   K   L   L   S   K   T   P   E   L   N
140                              150
```

FIG.7A

```
CTG GAT CAG TTC CAC GAC AAG ACC CCT TAT ACG ATT ATG TTT GGT CCA GAT   680
 L   D   Q   F   H   D   K   T   P   Y   T   I   M   F   G   P   D
             160                                     170

AAA TGT GGA GAA GAC TAT AAA CTG CAC TTC ATC TTC CGC CAC AAA AAC CCC   731
 K   C   G   E   D   Y   K   L   H   F   I   F   R   H   K   N   P
                             180                                 190

AAA ACA GGC GTA TAT GAA GAA AAG CAT GCT AAG AGG CCA GAT GCA GAT CTG   782
 K   T   G   V   Y   E   E   K   H   A   K   R   P   D   A   D   L
                                     200

AAG ACC TAT TTT ACT GAC AAG AAA ACA CAT CTT TAT ACA TTA ATC TTG AAT   833
 K   T   Y   F   T   D   K   K   T   H   L   Y   T   L   I   L   N
         210                         220

CCA GAT AAT AGT TTT GAA ATA CTA GTG GAC CAA TCT ATT GTG AAT AGT GGA   884
 P   D   N   S   F   E   I   L   V   D   Q   S   I   V   N   S   G
                         230                                 240

AAT TTA CTA AAT GAC ATG ACT CCT CCT GTA AAT CCT TCA CGT GAA ATT GAG   935
 N   L   L   N   D   M   T   P   P   V   N   P   S   R   E   I   E
                             250

GAC CCA GAA GAC CAG AAG CCT GAA GAT TGG GAT GAA AGA CCA AAA ATA CCA   986
 D   P   E   D   Q   K   P   E   D   W   D   E   R   P   K   I   P
             260                         270

GAT CCT GAT GCT GTC AAA CCA GAT GAC TGG AAT GAA GAT GCC CCT GCT AAG  1037
 D   P   D   A   V   K   P   D   D   W   N   E   D   A   P   A   K
                     280                                 290

ATT CCA GAT GAA GAA GCT ACG AAG CCT GAT GGC TGG TTA GAT GAT GAA CCC  1088
 I   P   D   E   E   A   T   K   P   D   G   W   L   D   D   E   P
                             300

GAA TAT GTA CCT GAT CCA GAT GCA GAG AAG CCA GAG GAT TGG GAT GAA GAT  1139
 E   Y   V   P   D   P   D   A   E   K   P   E   D   W   D   E   D
310                                              320
```

FIG.7B

```
ATG GAT GGA GAA TGG GAG GCT CCT CAG ATC GCC AAC CCT AAG TGT GAG TCG 1190
 M   D   G   E   W   E   A   P   Q   I   A   N   P   K   C   E   S
             330                                 340

GCC CCT GGG TGT GGT GTC TGG CAG CGA CCT ATG ATT GAC AAC CCT AAT TAT 1241
 A   P   G   C   G   V   W   Q   R   P   M   I   D   N   P   N   Y
                     350                                         360

AAG GGC AAA TGG AAG CCT CCC ATG ATT GAC AAT CCT AAC TAC CAG GGA ATC 1292
 K   G   K   W   K   P   P   M   I   D   N   P   N   Y   Q   G   I
                             370

TGG AAA CCC CGG AAG ATA CCA AAT CCG GAT TTC TTT GAA GAT CTG GAA CCT 1343
 W   K   P   R   K   I   P   N   P   D   F   F   E   D   L   E   P
             380                                 390

TTC AAA ATG ACT CCT TTT AGC GCT ATT GGT TTG GAA CTG TGG TCT ATG ACC 1394
 F   K   M   T   P   F   S   A   I   G   L   E   L   W   S   M   T
                 400                                         410

TCA GAC ATT TTT TTT GAC AAC TTT ATT GTT TGT GGG GAT CGA AGA GTA GTT 1445
 S   D   I   F   F   D   N   F   I   V   C   G   D   R   R   V   V
                             420

GAT GAT TGG GCC AAT GAT GGA TGG GGT CTG AAG AAA GCA GCT GAT GGG GCT 1496
 D   D   W   A   N   D   G   W   G   L   K   K   A   A   D   G   A
     430                                 440

GCC GAG CCA GGT GTG GTG GGG CAG ATG ATT GAG GCA GCT GAG GAG CGC CCG 1547
 A   E   P   G   V   V   G   Q   M   I   E   A   A   E   E   R   P
                 450                                 460

TGG CTC TGG GTG GTC TAC GTT TTG ACC GTA GCT CTG CCC GTG TTT CTT GTT 1598
 W   L   W   V   V   Y   V   L   T   V   A   L   P   V   F   L   V
                             470

ATC CTC TTC TGC TGC TCT GGA AAG AAA CAG TCA AGT CCT GTG GAG TAT AAG 1649
 I   L   F   C   C   S   G   K   K   Q   S   S   P   V   E   Y   K
480                                      490

AAG ACA GAC GCT CCT CAG CCA GAT GTG AAG GAG GAG GAA GAA GAA AAG GAA 1700
 K   T   D   A   P   Q   P   D   V   K   E   E   E   E   E   K   E
             500                                 510
```

FIG.7C

```
GAG GAA AAG GAC AAG GGC GAT GAG GAG GAG GAG GGC GAA GAA AAA CTT GAA  1751
 E   E   K   D   K   G   D   E   E   E   E   G   E   E   K   L   E
                         520                                 530

GAG AAG CAA AAA AGT GAT GCT GAA GAA GAT GGC GGC ACT GCC AGT CAA GAG  1802
 E   K   Q   K   S   D   A   E   E   D   G   G   T   A   S   Q   E
                         540

GAG GAC GAT AGG AAA CCT AAG GCA GAG GAG GAT GAA ATT TTG AAC AGA TCA  1853
 E   D   D   R   K   P   K   A   E   E   D   E   I   L   N   R   S
             550                             560

CCA AGA AAC AGA AAG CCA CGA AGA GAG TGA AACAATTTTAAGAACTTGAT         1903
 P   R   N   R   K   P   R   R   E  END
                 570             573
CTGTGATTTCCTCTCCCTCCTCCCCTTCCCCTGCAAGCATGGTCCTGGGAGAGGACCTGG         1963
CACACCTTAGGTTGAACTCAGAAAACCTCCAGACATCACCATCAACAGGTTCCAGTCGAA         2023
CACTAGCCCGTGTAATTTTAAACATCTAAGCAGTAAATAATTGCTGTTGTGAAATAAAGG         2083
ACCCTGTTTCTGTAGAAAGAAGGCATATAACATTAATAGTTGTGAAATGTAACATGAAGC         2143
AACTAACTTGTATTTTTTGTTTTGTTTTGTTTTTAAACATCTTTGTTTTTTAAAATAGAG         2203
TGATAGAACTTTGCCAGTCTTTAAAATCTTGGCTTAATTTAATATATTAATCTGTCCATG         2263
CAGAAATAACACCAACCTTTAGAAATGTTTGGGGGATGAATTGCAGTTTCTATAACCAAA         2323
TTTTTAAGTTTGGTATTATGAAACATTCAAGTGTTCTCTGTCCCTTAAAATTGATAATCA         2383
TTGTTTAAAGTGCAGTCATTTGTGGTTATAGTCTTGTTTTGCTTGCTTCCATCACCCAGT         2443
TCCTCCTAAGAAAACTGAGGAGATGGACTGGATGGAAGCCCAAATTATAAAAGGTTCTGT         2503
TTCAGTTATATTAAAAATAGATATACAGAAAGAAGAAACTTTTCCTCTTGGTGTTGGTTA         2563
GACCATACAGTGCGTGTGTTCTGTTGCCCTTGGTAGCAGCTCTGTTCCCAGACGGCTCTG         2623
CAGTCCGTTGAGGAGGTGGTATGATGTGGCATTCGGGCAGTCATGCTTCCACAACTGGGA         2683
GTGTCTGGGCTCCAGCCTTCCGGAGCAGGTGGCTGTTTGAGGAATGCTCCCAGGGCATGG         2743
GAGCTCCCAAGCAGACGCAGATGTTTTCATCACTTCCTCCACTGTGTTGACACTGTCTCC         2803
TTCCCAGTTGTCCCAGATCCCCAGCTTTCTCCTCTGCTATGCATTTTCTTCACAGCGCAC         2863
GTTGCAGTCCGTCACTGAAAATGATTATAAGCTCCGCATAGTGTTAAGCTTTATTGTGAT         2923
TAAGTGTATGTTTCTTCCTTCTTTAAGCAGACCCACACCTTTCCAGGGTCAAAGTACAGG         2983
ATAAGATACTGTCTTTCATTTTTATCCATTTCTTTTGCTCTGTGTCAAGACTTGAAAAGT         3043
CTCAGCCAGAGGTGAGCCAATTCAGAATCTGTAATTGAACACAGGCTTAAAGTATTT 3'      3100
```

FIG. 7D

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 3100 base pairs
        ( B ) TYPE: nucleic acid ( C ) STRANDEDNESS: single
( D ) TOPOLOGY: linear ( i i ) MOLECULE TYPE: cDNA ( i x ) FEATURE:
( A ) NAME/KEY: CDS
( B ) LOCATION: 102..1883

( x i ) SEQUENCE DESCRIPTION: SEQ ID NO:1:

| | | | | | |
|---|---|---|---|---|---|
| CGCGGCTCGT GACGGTCGGG CAGCCTCCGC TGCTGTCTCC ACTGCAGCGC GGGCCGGGCG | | | | | 60 |
| TGCGGGCGGG TGGAGGCGCG GGCCGCGCAC GACTCGAGAT C ATG GAA GGG AAA<br>Met Glu Gly Lys<br>1 | | | | | 113 |

| TGG | CTG | CTG | TGT | ATG | TTA | CTG | GTC | CTT | GGA | ACT | ACT | ATT | GTT | CAG | GCT | 161 |
|---|---|---|---|---|---|---|---|---|---|---|---|---|---|---|---|---|
| Trp<br>5 | Leu | Leu | Cys | Met | Leu<br>10 | Leu | Val | Leu | Gly | Thr<br>15 | Thr | Ile | Val | Gln | Ala<br>20 | |
| CAT | GAA | GGA | CAT | GAT | GAT | GAT | ATG | ATT | GAT | ATT | GAG | GAC | GAC | CTC | GAT | 209 |
| His | Glu | Gly | His<br>25 | Asp | Asp | Asp | Met | Ile<br>30 | Asp | Ile | Glu | Asp | Asp<br>35 | Leu | Asp | |
| GAT | GTT | ATT | GAA | GAG | GTA | GAA | GAC | TCC | AAA | TCA | AAA | CCA | GAT | ACC | AGC | 257 |
| Asp | Val | Ile | Glu<br>40 | Glu | Val | Glu | Asp | Ser<br>45 | Lys | Ser | Lys | Pro | Asp<br>50 | Thr | Ser | |
| GCT | CCT | ACA | TCT | CCA | AAG | GCT | ACC | TAT | AAA | GCT | CCA | GTT | CCT | TCC | GGG | 305 |
| Ala | Pro | Thr<br>55 | Ser | Pro | Lys | Ala | Thr<br>60 | Tyr | Lys | Ala | Pro | Val<br>65 | Pro | Ser | Gly | |
| GAA | GTG | TAT | TTT | GCT | GAT | TCC | TTT | GAC | AGA | GGA | ACT | CTG | TCA | GGG | TGG | 353 |
| Glu | Val<br>70 | Tyr | Phe | Ala | Asp | Ser<br>75 | Phe | Asp | Arg | Gly | Thr<br>80 | Leu | Ser | Gly | Trp | |
| ATT | TTA | TCA | AAA | GCC | AAG | AAG | GAT | GAC | ACT | GAT | GAT | GAA | ATT | GCC | AAA | 401 |
| Ile<br>85 | Leu | Ser | Lys | Ala | Lys<br>90 | Lys | Asp | Asp | Thr | Asp<br>95 | Asp | Glu | Ile | Ala | Lys<br>100 | |
| TAT | GAC | GGA | AAG | TGG | GAG | GTA | GAT | GAA | ATG | AAG | GAA | ACA | AAG | CTC | CCA | 449 |
| Tyr | Asp | Gly | Lys | Trp<br>105 | Glu | Val | Asp | Glu | Met<br>110 | Lys | Glu | Thr | Lys | Leu<br>115 | Pro | |
| GGT | GAT | AAA | GGG | CTT | GTG | TTG | ATG | TCT | CGG | GCC | AAG | CAT | CAT | GCC | ATC | 497 |
| Gly | Asp | Lys | Gly<br>120 | Leu | Val | Leu | Met | Ser<br>125 | Arg | Ala | Lys | His | His<br>130 | Ala | Ile | |
| TCT | GCA | AAA | CTC | AAC | AAG | CCC | TTC | CTG | TTT | GAT | ACC | AAG | CCT | CTC | ATT | 545 |
| Ser | Ala | Lys<br>135 | Leu | Asn | Lys | Pro | Phe<br>140 | Leu | Phe | Asp | Thr | Lys<br>145 | Pro | Leu | Ile | |
| GTT | CAG | TAT | GAG | GTT | AAT | TTC | CAA | AAT | GGA | ATA | GAA | TGT | GGT | GGT | GCC | 593 |
| Val | Gln | Tyr<br>150 | Glu | Val | Asn | Phe | Gln<br>155 | Asn | Gly | Ile | Glu | Cys<br>160 | Gly | Gly | Ala | |
| TAT | GTG | AAA | CTG | CTT | TCC | AAA | ACC | CCC | GAA | CTC | AAC | CTG | GAT | CAG | TTC | 641 |
| Tyr | Val | Lys | Leu<br>165 | Leu | Ser | Lys | Thr | Pro<br>170 | Glu | Leu | Asn | Leu | Asp<br>175 | Gln | Phe<br>180 | |
| CAC | GAC | AAG | ACC | CCT | TAT | ACG | ATT | ATG | TTT | GGT | CCA | GAT | AAA | TGT | GGA | 689 |
| His | Asp | Lys | Thr | Pro<br>185 | Tyr | Thr | Ile | Met | Phe<br>190 | Gly | Pro | Asp | Lys | Cys<br>195 | Gly | |
| GAA | GAC | TAT | AAA | CTG | CAC | TTC | ATC | TTC | CGC | CAC | AAA | AAC | CCC | AAA | ACA | 737 |
| Glu | Asp | Tyr | Lys<br>200 | Leu | His | Phe | Ile | Phe<br>205 | Arg | His | Lys | Asn | Pro<br>210 | Lys | Thr | |
| GGC | GTA | TAT | GAA | GAA | AAG | CAT | GCT | AAG | AGG | CCA | GAT | GCA | GAT | CTG | AAG | 785 |
| Gly | Val | Tyr<br>215 | Glu | Glu | Lys | His | Ala<br>220 | Lys | Arg | Pro | Asp | Ala<br>225 | Asp | Leu | Lys | |
| ACC | TAT | TTT | ACT | GAC | AAG | AAA | ACA | CAT | CTT | TAT | ACA | TTA | ATC | TTG | AAT | 833 |
| Thr | Tyr<br>230 | Phe | Thr | Asp | Lys | Lys<br>235 | Thr | His | Leu | Tyr | Thr<br>240 | Leu | Ile | Leu | Asn | |
| CCA | GAT | AAT | AGT | TTT | GAA | ATA | CTA | GTG | GAC | CAA | TCT | ATT | GTG | AAT | AGT | 881 |
| Pro<br>245 | Asp | Asn | Ser | Phe | Glu<br>250 | Ile | Leu | Val | Asp | Gln<br>255 | Ser | Ile | Val | Asn | Ser<br>260 | |

| | | | | | | | | | | | | | | | | |
|---|---|---|---|---|---|---|---|---|---|---|---|---|---|---|---|---|
| GGA | AAT | TTA | CTA | AAT | GAC | ATG | ACT | CCT | CCT | GTA | AAT | CCT | TCA | CGT | GAA | 929 |
| Gly | Asn | Leu | Leu | Asn | Asp | Met | Thr | Pro | Pro | Val | Asn | Pro | Ser | Arg | Glu | |
| | | | 265 | | | | | 270 | | | | | 275 | | | |
| ATT | GAG | GAC | CCA | GAA | GAC | CAG | AAG | CCT | GAA | GAT | TGG | GAT | GAA | AGA | CCA | 977 |
| Ile | Glu | Asp | Pro | Glu | Asp | Gln | Lys | Pro | Glu | Asp | Trp | Asp | Glu | Arg | Pro | |
| | | | 280 | | | | 285 | | | | | 290 | | | | |
| AAA | ATA | CCA | GAT | CCT | GAT | GCT | GTC | AAA | CCA | GAT | GAC | TGG | AAT | GAA | GAT | 1025 |
| Lys | Ile | Pro | Asp | Pro | Asp | Ala | Val | Lys | Pro | Asp | Asp | Trp | Asn | Glu | Asp | |
| | | 295 | | | | | 300 | | | | | 305 | | | | |
| GCC | CCT | GCT | AAG | ATT | CCA | GAT | GAA | GAA | GCT | ACG | AAG | CCT | GAT | GGC | TGG | 1073 |
| Ala | Pro | Ala | Lys | Ile | Pro | Asp | Glu | Glu | Ala | Thr | Lys | Pro | Asp | Gly | Trp | |
| | 310 | | | | | 315 | | | | | 320 | | | | | |
| TTA | GAT | GAT | GAA | CCC | GAA | TAT | GTA | CCT | GAT | CCA | GAT | GCA | GAG | AAG | CCA | 1121 |
| Leu | Asp | Asp | Glu | Pro | Glu | Tyr | Val | Pro | Asp | Pro | Asp | Ala | Glu | Lys | Pro | |
| 325 | | | | | 330 | | | | | 335 | | | | | 340 | |
| GAG | GAT | TGG | GAT | GAA | GAT | ATG | GAT | GGA | GAA | TGG | GAG | GCT | CCT | CAG | ATC | 1169 |
| Glu | Asp | Trp | Asp | Glu | Asp | Met | Asp | Gly | Glu | Trp | Glu | Ala | Pro | Gln | Ile | |
| | | | | 345 | | | | | 350 | | | | | 355 | | |
| GCC | AAC | CCT | AAG | TGT | GAG | TCG | GCC | CCT | GGG | TGT | GGT | GTC | TGG | CAG | CGA | 1217 |
| Ala | Asn | Pro | Lys | Cys | Glu | Ser | Ala | Pro | Gly | Cys | Gly | Val | Trp | Gln | Arg | |
| | | | 360 | | | | | 365 | | | | | 370 | | | |
| CCT | ATG | ATT | GAC | AAC | CCT | AAT | TAT | AAG | GGC | AAA | TGG | AAG | CCT | CCC | ATG | 1265 |
| Pro | Met | Ile | Asp | Asn | Pro | Asn | Tyr | Lys | Gly | Lys | Trp | Lys | Pro | Pro | Met | |
| | | 375 | | | | | 380 | | | | | 385 | | | | |
| ATT | GAC | AAT | CCT | AAC | TAC | CAG | GGA | ATC | TGG | AAA | CCC | CGG | AAG | ATA | CCA | 1313 |
| Ile | Asp | Asn | Pro | Asn | Tyr | Gln | Gly | Ile | Trp | Lys | Pro | Arg | Lys | Ile | Pro | |
| | | 390 | | | | | 395 | | | | | 400 | | | | |
| AAT | CCG | GAT | TTC | TTT | GAA | GAT | CTG | GAA | CCT | TTC | AAA | ATG | ACT | CCT | TTT | 1361 |
| Asn | Pro | Asp | Phe | Phe | Glu | Asp | Leu | Glu | Pro | Phe | Lys | Met | Thr | Pro | Phe | |
| 405 | | | | | 410 | | | | | 415 | | | | | 420 | |
| AGC | GCT | ATT | GGT | TTG | GAA | CTG | TGG | TCT | ATG | ACC | TCA | GAC | ATT | TTT | TTT | 1409 |
| Ser | Ala | Ile | Gly | Leu | Glu | Leu | Trp | Ser | Met | Thr | Ser | Asp | Ile | Phe | Phe | |
| | | | | 425 | | | | | 430 | | | | | 435 | | |
| GAC | AAC | TTT | ATT | GTT | TGT | GGG | GAT | CGA | AGA | GTA | GTT | GAT | GAT | TGG | GCC | 1457 |
| Asp | Asn | Phe | Ile | Val | Cys | Gly | Asp | Arg | Arg | Val | Val | Asp | Asp | Trp | Ala | |
| | | | 440 | | | | | 445 | | | | | 450 | | | |
| AAT | GAT | GGA | TGG | GGT | CTG | AAG | AAA | GCA | GCT | GAT | GGG | GCT | GCC | GAG | CCA | 1505 |
| Asn | Asp | Gly | Trp | Gly | Leu | Lys | Lys | Ala | Ala | Asp | Gly | Ala | Ala | Glu | Pro | |
| | | 455 | | | | | 460 | | | | | 465 | | | | |
| GGT | GTG | GTG | GGG | CAG | ATG | ATT | GAG | GCA | GCT | GAG | GAG | CGC | CCG | TGG | CTC | 1553 |
| Gly | Val | Val | Gly | Gln | Met | Ile | Glu | Ala | Ala | Glu | Glu | Arg | Pro | Trp | Leu | |
| | | 470 | | | | | 475 | | | | | 480 | | | | |
| TGG | GTG | GTC | TAC | GTT | TTG | ACC | GTA | GCT | CTG | CCC | GTG | TTT | CTT | GTT | ATC | 1601 |
| Trp | Val | Val | Tyr | Val | Leu | Thr | Val | Ala | Leu | Pro | Val | Phe | Leu | Val | Ile | |
| 485 | | | | | 490 | | | | | 495 | | | | | 500 | |
| TCT | TTC | TGC | TGC | TCT | GGA | AAG | AAA | CAG | TCA | AGT | CCT | GTG | GAG | TAT | AAG | 1649 |
| Ser | Phe | Cys | Cys | Ser | Gly | Lys | Lys | Gln | Ser | Ser | Pro | Val | Glu | Tyr | Lys | |
| | | | | 505 | | | | | 510 | | | | | 515 | | |
| AAG | ACA | GAC | GCT | CCT | CAG | CCA | GAT | GTG | AAG | GAG | GAG | GAA | GAA | GAA | AAG | 1697 |
| Lys | Thr | Asp | Ala | Pro | Gln | Pro | Asp | Val | Lys | Glu | Glu | Glu | Glu | Glu | Lys | |
| | | | 520 | | | | | 525 | | | | | 530 | | | |
| GAA | GAG | GAA | AAG | GAC | AAG | GGC | GAT | GAG | GAG | GAG | GAG | GGC | GAA | GAA | AAA | 1745 |
| Glu | Glu | Glu | Lys | Asp | Lys | Gly | Asp | Glu | Glu | Glu | Glu | Gly | Glu | Glu | Lys | |
| | | 535 | | | | | 540 | | | | | 545 | | | | |
| CTT | GAA | GAG | AAG | CAA | AAA | AGT | GAT | GCT | GAA | GAA | GAT | GGC | GGC | ACT | GCC | 1793 |
| Leu | Glu | Glu | Lys | Gln | Lys | Ser | Asp | Ala | Glu | Glu | Asp | Gly | Gly | Thr | Ala | |
| | | 550 | | | | | 555 | | | | | 560 | | | | |
| AGT | CAA | GAG | GAG | GAC | GAT | AGG | AAA | CCT | AAG | GCA | GAG | GAG | GAT | GAA | ATT | 1841 |
| Ser | Gln | Glu | Glu | Asp | Asp | Arg | Lys | Pro | Lys | Ala | Glu | Glu | Asp | Glu | Ile | |
| 565 | | | | | 570 | | | | | 575 | | | | | 580 | |

```
TTG AAC AGA TCA CCA AGA AAC AGA AAG CCA CGA AGA GAG TGAAACAATT      1890
Leu Asn Arg Ser Pro Arg Asn Arg Lys Pro Arg Arg Glu
            585                 590

TTAAGAACTT GATCTGTGAT TTCCTCTCCC TCCTCCCCTT CCCCTGCAAG CATGGTCCTG   1950
GGAGAGGACC TGGCACACCT TAGGTTGAAC TCAGAAAACC TCCAGACATC ACCATCAACA   2010
GGTTCCAGTC GAACACTAGC CCGTGTAATT TTAAACATCT AAGCAGTAAA TAATTGCTGT   2070
TGTGAAATAA AGGACCCTGT TTGTGTAGAA AGAAGGCATA TAACATTAAT AGTTGTGAAA   2130
TGTAACATGA AGCAACTAAC TTGTATTTTT TGTTTTGTTT TGTTTTAAA CATCTTTGTT    2190
TTTTAAAATA GAGTGATAGA ACTTTGCCAG TCTTTAAAAT CTTGGCTTAA TTTAATATAT   2250
TAATCTGTCC ATGCAGAAAT AACACCAACC TTTAGAAATG TTTGGGGGAT GAATTGCAGT   2310
TTCTATAACC AAATTTTTAA GTTGGTATT ATGAAACATT CAAGTGTTCT CTGTCCCTTA    2370
AAATTGATAA TCATTGTTTA AGTGCAGTC ATTTGTGGTT ATAGTCTTGT TTGCTTGCT     2430
TCCATCACCC AGTTCCTCCT AAGAAAACTG AGGAGATGGA CTGGATGGAA GCCCAAATTA   2490
TAAAAGGTTC TGTTTCAGTT ATATTAAAAA TAGATATACA GAAAGAAGAA ACTTTTCCTC   2550
TTGGTGTTGG TTAGACCATA CAGTGCGTGT GTTCTGTTGC CCTTGGTAGC AGCTCTGTTC   2610
CCAGACGGCT CTGCAGTCCG TTGAGGAGGT GGTATGATGT GGCATTCGGG CAGTCATGCT   2670
TCCACAACTG GGAGTGTCTG GGCTCCAGCC TTCCGGAGCA GGTGGCTGTT TGAGGAATGC   2730
TCCCAGGGCA TGGGAGCTCC CAAGCAGACG CAGATGTTTT CATCACTTCC TCCACTGTGT   2790
TGACACTGTC TCCTTCCCAG TTGTCCCAGA TCCCCAGCTT TCTCCTCTGC TATGCATTTT   2850
CTTCACAGCG CACGTTGCAG TCCGTCACTG AAAATGATTA TAAGCTCCGC ATAGTGTTAA   2910
GCTTTATTGT GATTAAGTGT ATGTTCTTC CTTCTTTAAG CAGACCCACA CCTTTCCAGG    2970
GTCAAAGTAC AGGATAAGAT ACTGTCTTTC ATTTTTATCC ATTTCTTTTG CTCTGTGTCA   3030
AGACTTGAAA AGTCTCAGCC AGAGGTGAGC CAATTCAGAA TCTGTAATTG AACACAGGCT   3090
TAAAGTATTT                                                          3100
```

( 2 ) INFORMATION FOR SEQ ID NO:2:

( i ) SEQUENCE CHARACTERISTICS:
        ( A ) LENGTH: 593 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met Glu Gly Lys Trp Leu Leu Cys Met Leu Leu Val Leu Gly Thr Thr
 1               5                  10                  15

Ile Val Gln Ala His Glu Gly His Asp Asp Met Ile Asp Ile Glu
                20                  25                  30

Asp Asp Leu Asp Asp Val Ile Glu Val Glu Asp Ser Lys Ser Lys
                35                  40                  45

Pro Asp Thr Ser Ala Pro Thr Ser Pro Lys Ala Thr Tyr Lys Ala Pro
 50                  55                  60

Val Pro Ser Gly Glu Val Tyr Phe Ala Asp Ser Phe Asp Arg Gly Thr
 65                  70                  75                  80

Leu Ser Gly Trp Ile Leu Ser Lys Ala Lys Lys Asp Asp Thr Asp Asp
                85                  90                  95

Glu Ile Ala Lys Tyr Asp Gly Lys Trp Glu Val Asp Glu Met Lys Glu
                100                 105                 110
```

-continued

| | | | | | | | | | | | | | | |
|---|---|---|---|---|---|---|---|---|---|---|---|---|---|---|
|Thr|Lys|Leu 115|Pro|Gly|Asp|Lys|Gly 120|Leu|Val|Leu|Met|Ser 125|Arg|Ala|Lys|
|His|His 130|Ala|Ile|Ser|Ala|Lys 135|Leu|Asn|Lys|Pro|Phe 140|Leu|Phe|Asp|Thr|
|Lys 145|Pro|Leu|Ile|Val|Gln 150|Tyr|Glu|Val|Asn|Phe 155|Gln|Asn|Gly|Ile|Glu 160|
|Cys|Gly|Gly|Ala|Tyr 165|Val|Lys|Leu|Leu|Ser 170|Lys|Thr|Pro|Glu|Leu 175|Asn|
|Leu|Asp|Gln|Phe 180|His|Asp|Lys|Thr|Pro 185|Tyr|Thr|Ile|Met|Phe 190|Gly|Pro|
|Asp|Lys|Cys 195|Gly|Glu|Asp|Tyr|Lys 200|Leu|His|Phe|Ile|Phe 205|Arg|His|Lys|
|Asn|Pro 210|Lys|Thr|Gly|Val|Tyr 215|Glu|Glu|Lys|His|Ala 220|Lys|Arg|Pro|Asp|
|Ala 225|Asp|Leu|Lys|Thr|Tyr 230|Phe|Thr|Asp|Lys|Lys 235|Thr|His|Leu|Tyr|Thr 240|
|Leu|Ile|Leu|Asn|Pro 245|Asp|Asn|Ser|Phe|Glu 250|Ile|Leu|Val|Asp|Gln 255|Ser|
|Ile|Val|Asn|Ser 260|Gly|Asn|Leu|Leu|Asn 265|Asp|Met|Thr|Pro 270|Pro|Val|Asn|
|Pro|Ser|Arg 275|Glu|Ile|Glu|Asp|Pro 280|Glu|Asp|Gln|Lys|Pro 285|Glu|Asp|Trp|
|Asp 290|Glu|Arg|Pro|Lys|Ile 295|Pro|Asp|Pro|Asp|Ala 300|Val|Lys|Pro|Asp|Asp|
|Trp 305|Asn|Glu|Asp|Ala|Pro 310|Ala|Lys|Ile|Pro|Asp 315|Glu|Glu|Ala|Thr|Lys 320|
|Pro|Asp|Gly|Trp|Leu 325|Asp|Asp|Glu|Pro|Glu 330|Tyr|Val|Pro|Asp|Pro 335|Asp|
|Ala|Glu|Lys|Pro 340|Glu|Asp|Trp|Asp|Glu 345|Asp|Met|Asp|Gly|Glu 350|Trp|Glu|
|Ala|Pro|Gln 355|Ile|Ala|Asn|Pro|Lys 360|Cys|Glu|Ser|Ala|Pro 365|Gly|Cys|Gly|
|Val|Trp 370|Gln|Arg|Pro|Met|Ile 375|Asp|Asn|Pro|Asn|Tyr 380|Lys|Gly|Lys|Trp|
|Lys 385|Pro|Pro|Met|Ile|Asp 390|Asn|Pro|Asn|Tyr|Gln 395|Gly|Ile|Trp|Lys|Pro 400|
|Arg|Lys|Ile|Pro|Asn 405|Pro|Asp|Phe|Phe|Glu 410|Asp|Leu|Glu|Pro|Phe 415|Lys|
|Met|Thr|Pro|Phe 420|Ser|Ala|Ile|Gly|Leu 425|Glu|Leu|Trp|Ser|Met 430|Thr|Ser|
|Asp|Ile|Phe|Phe 435|Asp|Asn|Phe|Ile 440|Val|Cys|Gly|Asp|Arg 445|Arg|Val|Val|
|Asp|Asp 450|Trp|Ala|Asn|Asp|Gly 455|Trp|Gly|Leu|Lys|Lys 460|Ala|Ala|Asp|Gly|
|Ala 465|Ala|Glu|Pro|Gly|Val 470|Val|Gly|Gln|Met|Ile 475|Glu|Ala|Ala|Glu|Glu 480|
|Arg|Pro|Trp|Leu|Trp 485|Val|Val|Tyr|Val|Leu 490|Thr|Val|Ala|Leu|Pro 495|Val|
|Phe|Leu|Val|Ile 500|Ser|Phe|Cys|Cys|Ser 505|Gly|Lys|Lys|Gln|Ser 510|Ser|Pro|
|Val|Glu|Tyr 515|Lys|Lys|Thr|Asp|Ala 520|Pro|Gln|Pro|Asp|Val 525|Lys|Glu|Glu|
|Glu|Glu|Glu 530|Lys|Glu|Glu|Glu|Lys 535|Asp|Lys|Gly|Asp|Glu 540|Glu|Glu|Glu|

-continued

```
Gly Glu Glu Lys Leu Glu Glu Lys Gln Lys Ser Asp Ala Glu Glu Asp
545                 550             555                 560

Gly Gly Thr Ala Ser Gln Glu Glu Asp Arg Lys Pro Lys Ala Glu
            565             570             575

Glu Asp Glu Ile Leu Asn Arg Ser Pro Arg Asn Arg Lys Pro Arg Arg
            580             585             590

Glu
```

METHODS OF DETECTION AND TREATMENT OF PROTEIN TRAFFICKING DISORDERS AND INCREASING SECRETORY PROTEIN PRODUCTION

CROSS-REFERENCE TO RELATED APPLICATION

This application is a continuation-in-part application to Ser. No. 08/112,395, filed Aug. 26, 1993, now abandoned.

TECHNICAL FIELD

The present invention is generally directed toward methods of treating and diagnosing protein trafficking disorders and altering secretory protein production. More specifically, the present invention is directed toward compositions and methods of treating and diagnosing protein trafficking disorders and altering secretory protein production by controlling calnexin activity.

BACKGROUND OF THE INVENTION

The endoplasmic reticulum (ER) functions in the translocation of proteins, cleavage of signal peptides, protein folding, core glycosylation, assembly of oligomers, degradation of misfolded secretory proteins, and storage of calcium in the cell. It facilitates these activities through the use of a number of different enzymes and "molecular chaperones." BiP is a known molecular chaperone in the ER's luminal pathway. However, the futile search for an association of secretory proteins in HepG2 cells with BiP has provided a strong indicia that more than one pathway is present (Lodish, *J. Biol. Chem.* 263:2107–2110, 1988). To date, efforts to elucidate the second pathway deemed the "membrane pathway" have been unsuccessful.

Elucidation of the nature of the membrane pathway and its components is of primary importance to treatment of protein trafficking disorders such as cystic fibrosis, juvenile pulmonary emphysema, Tay-Sachs disease, congenital sucrose isomaltase deficiency, and familial hypercholesterolaemia. These protein trafficking disorders and others may be caused by alteration of any aspect of the translocation assembly, or the proteins associated therewith, causing them to be inappropriately retained in the ER.

In view of the lack of current therapies to successfully control all protein trafficking disorders, it is evident that there exists a need for new and additional therapeutic agents and methods to treat these disorders. The present invention fulfills these needs, and further provides other related advantages.

SUMMARY OF THE INVENTION

The present invention is generally directed towards methods of treating and diagnosing protein trafficking disorders and controlling secretory protein production.

In one aspect, the present invention involves methods of increasing secretory protein production in a biological preparation, comprising administering a calnexin suppressor agent to a biological preparation in an amount effective to increase secretory protein production.

Another aspect of the present invention involves agents which decrease calnexin associations for use in the manufacure of a medicament for increasing secretory protein production in a warm-blooded animal.

Another aspect of the present invention involves compositions that include an agent which decrease calnexin activity for use in the manufacture of a medicament for treating a warm-blooded animal for protein trafficking disorders which require reduction of calnexin associations.

Another aspect of the present invention involves compositions that include an agent which stimulates calnexin activity for use in the manufacture of a medicament for treating a warm-blooded animal for a protein trafficking disorder which require stimulation of calnexin associations.

Another aspect of the present invention involves conjugates comprising agents linked to moieties which target the conjugates to the endosplasmic reticulum for use in the manufacture of a medicament for treating a warm-blooded animal for a protein trafficking disorder.

Another aspect of the present invention involves methods of diagnosing a protein trafficking disorder in a waxenblooded animal, comprising exposing an anticalnexin antibody, containing a reporter group, to the ER of a warm-blooded animal under conditions and for a time sufficient to permit binding to calnexin, and detecting the amount of calnexin and determining therefrom the presence of a protein trafficking disorder.

Another aspect of the present invention involves methods of diagnosing a protein trafficking disorder in a biological preparation, comprising exposing an anticalnexin antibody, containing a reporter group, to the biological preparation under conditions and for a time sufficient to permit binding to calnexin, and detecting the amount of calnexin and determining therefrom the presence of as protein trafficking disorder.

These and other aspects of the present invention will become evident upon reference to the following detailed description and attached drawings. In addition, various references are set forth which describe in more detail certain procedures and/or compositions, and are hereby incorporated by reference in their entirety.

BRIEF DESCRIPTION OF THE DRAWINGS

FIG. 1 Association of newly synthesized proteins with calnexin in HepG2 cells.

FIG. 1a. HepG2 cells were labeled with 50 µCi//ml Trans $^{35}$S-label for 30 minutes followed by lysis and immunoprecipitation with anti-α 1-antitrypsin antibody (lanes 1 and 2) and either untreated (lane 1) or treated (lane 2) with endo H. Cell lysates were immunoprecipitated with anti-calnexin antibody under denaturing (lane 3) or non-denaturing conditions (lane 4). After immunoprecipitation with anti-calnexin antibody under non-denaturing conditions, coprecipitated proteins were eluted from protein A-agarose beads with SDS. Sequential immunoprecipitations were carded out with anti-α1-antitrypsin (lane 5); anti-α1-antichymotrypsin (lane 6); anti-transferrin (lane 7); anti-C3 (lane 8); anti-apoβ-100 (lane 9); anti-α-fetoprotein (lane 10) and anti-albumin antibodies (lane 11). Lysates immunoprecipitated directly with anti-albumin antibody revealed a major band corresponding to the expected mobility of albumin (lane 12.)

FIG. 1b. HepG2 cells were incubated at 37° C. in the presence of 10 µg/ml tunicamycin for 3 h., and then labeled with 50 µCi/ml Tran$^{35}$S-label for 10 minutes in the presence (lanes 2, 4 and 6) of 10 µg/ml tunicamycin (Boehringer Mannheim). Lanes 1, 3, 5 did not receive tunicamycin treatment. The cell lysates were immunoprecipitated with anti-α1-antitrypsin (lanes 1 and 2); anti-transferrin (lanes 3 and 4); and anti-calnexin (lanes 5, 6) under non-denaturing conditions. Immunoprecipitates were analyzed by SDS-PAGE. The mobilities of molecular mass markers (duping EN) are indicated to the left of the gels.

FIG. 3. Kinetics of association of newly synthesized secretory proteins with calnexin in HepG2 cells.

FIG. 5. Association of incompletely folded transferrin with calnexin.

FIGS. 7A–7D. A representative Calnexin DNA sequence as disclosed in Wada et al., *J. Biol. Chem.*, 266(29):19599–19610 (1991).

DETAILED DESCRIPTION OF THE INVENTION

Prior to setting forth this invention it may be helpful to first define certain terms that will be used herein.

"Protein trafficking disorder" refers to a disorder which affects secretory protein translocation, folding, or assembly in the ER. Representative examples of protein trafficking disorders include familial hypercholesterolaemia, cystic fibrosis, Tay-Sachs disease, congenital sucrose isomaltase deficiency, and juvenile pulmonary emphysema.

"Secretory protein" refers to all N-linked glycosylated proteins and unfolded proteins processed through the ER, including all coagulation factors, all blood factors, all hormone and growth factor receptors and all ion channels including, by way of example, cystic fibrosis chloride channels and there are nicotinic and muscarinic acetylcholine receptors.

"Biological preparation" refers to any animal cell or tissue ex vivo. Suitable preparations include, by way of example, HepG2 cells, COS cells, 293 cells, and ATT20 cells.

"Molecular chaperone" refers to the class of proteins which stabilize unfolded or partially folded structures, prevent the formation of inappropriate intra- or interchain interactions, or interact with protein molecules to promote the rearrangement of protein-protein interactions in oligomeric structures.

"Calnexin association" refers to the association, including covalent and non-covalent binding, of calnexin to a secretory protein.

The present invention provides methods and compositions directed to the regulation of secretory protein production and the treatment and diagnosis of protein trafficking disorders. The membrane pathway of the endoplasmic reticulum (ER) constitutes both a quality control and a translocation apparatus. Specifically, this apparatus is designed to ensure the functional integrity of secretory proteins and regulate their transport through the membrane. It is comprised of a complex of four integral membrane proteins, a phosphoprotein (pp90), a phosphoglycoprotein (pgp35), and two non-phosphorylated glycoproteins (gp25H and gp25L). The latter three proteins have been identified as signal sequence receptors SSRα (pgp35), SSRβ (gp25H), and a non-phosphorylated glycoprotein (gp25L). The phosphoprotein (pp90) represents calnexin. (The calnexin sequence is elucidated in FIG. 7.)

Figure 6:
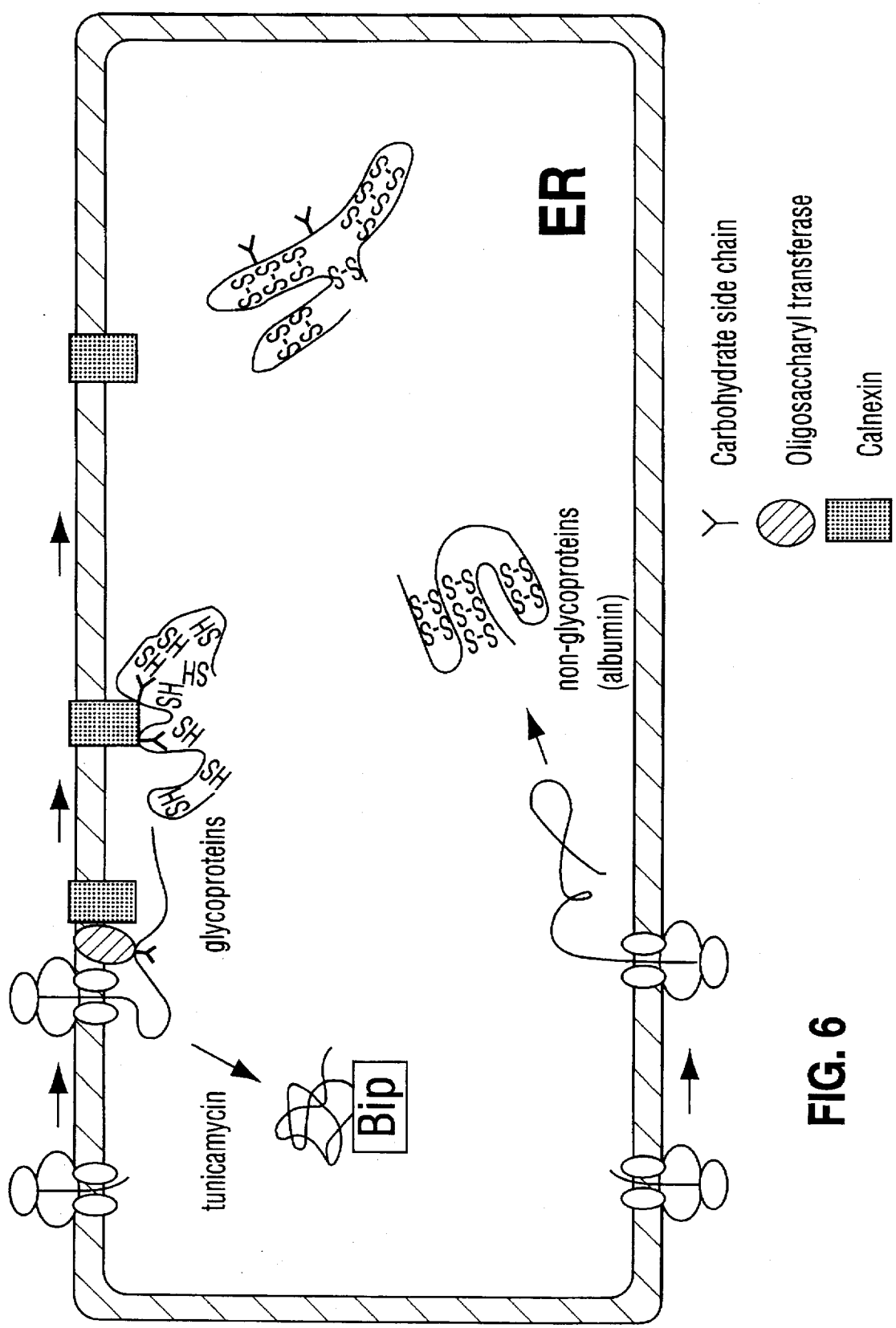
FIG. 6. Selectivity of calnexin for incompletely folded glycoproteins. Shortly after translocation, glycosylated proteins are presented to calnexin via oligosaccharyl transferase where protein folding, catalyzed by protein folding enzymes, occurs coincident with glycoprotein dissociation from calnexin (membrane associated pathway). Tunicamycin treatment prevents presentation to calnexin and may lead to protein misfolding and BiP association or folding by other ER luminal chaperones and secretion. Non-glycosylated proteins, e.g., albumin, are presented directly to the ER lumen where soluble resident chaperones may organize their folding with ER luminal protein folding enzymes.

Secretory proteins are divided between the luminal and membrane pathways by glycosylation. Glycosylation of nascent proteins leads to presentation to the membrane pathway while non-glycosylated proteins apparently follow the luminal pathway. (FIG. 6). Under normal conditions, some glycoproteins fold more rapidly on the membrane associated pathway with tunicamycin treatment leading to misfolding and inhibition of the rate of protein transport.

Calnexin is a molecular chaperone which selectively associates in a transient fashion with newly synthesized monomeric glycoproteins and is thus active in the membrane pathway. Calnexin associates with glycoproteins and incompletely folded secretory proteins. Dissociation of glycoproteins from calnexin occurs at different rates and is related to the time taken for their folding. This results in large differences and the rates of transport from the ER to the Golgi apparatus, with the rate limiting step governed by the time spent in the ER in association with calnexin.

Figure 2:
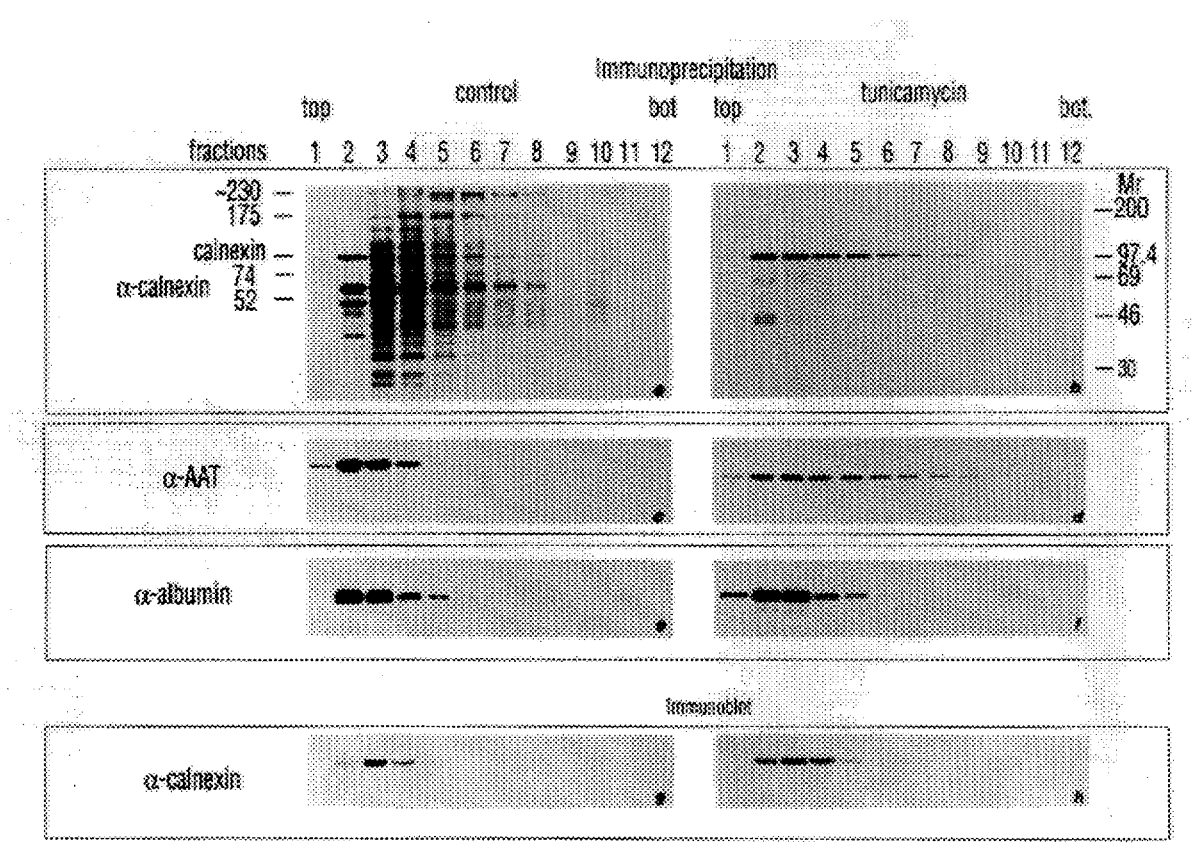
FIG. 2. Sucrose density gradient fractionation of calnexin-associated proteins. HepG2 cells without (a, c, e, and g) or with tunicamycin treatment for 3 h (b, d, f, and h) were radiolabeled for 10 minutes and then lysed in 2% cholate/HBS buffer. After centrifugation (100,000×g, 20 minutes), supernatants were loaded onto a 5%-30% (w/v) sucrose density gradient containing 50 mM Hepes-NaOH, pH 7.5, 0.2M NaCl, 0.3% cholate and centrifuged at 180,000×g for 15 h. Fractions were immunoprecipitated under non-denaturing conditions with anti-calnexin (a and b), anti-α 1-antitrypsin (c and d) or anti-albumin antibodies (e and f). g and h are immunoblots of the fractions probed with anti-calnexin antibody.

Calnexin, as molecular chaperone in the membrane pathway, is thus distinguishable from BiP, as a molecular chaperone in the luminal pathway. (FIGS. 1, 2, and 6). The differences are demonstrated by stress treatment. Stress conditions, such as heat shock or tunicamycin treatment, greatly stimulate the interaction of BiP with substrate proteins. However, neither treatment stimulates the association of calnexin with substrate proteins. In addition, BiP associated proteins usually form aggregates, whereas calnexin associated proteins do not. This can be observed by sucrose gradient centrifugation. (FIG. 2).

Only incompletely folded intermediates of transferrin, devoid of interchain disulphide bonds, are associated with calnexin although the interchain disulphide bonded species existed after maturation. (FIG. 4a). Such interchain aggregates have been observed in other studies on proteins folding in vivo and under defined conditions have been shown to be BiP associated. Thus, calnexin recognizes different features in secretory proteins that those recognized by BiP.

As noted above, one aspect of the present invention concerns increasing production of secretory proteins in either a biological preparation or a warm-blooded animal. As disclosed in the present invention, increase in the release of secretory proteins from the ER can be controlled by regulation of calnexin activity.

Figure 3A:
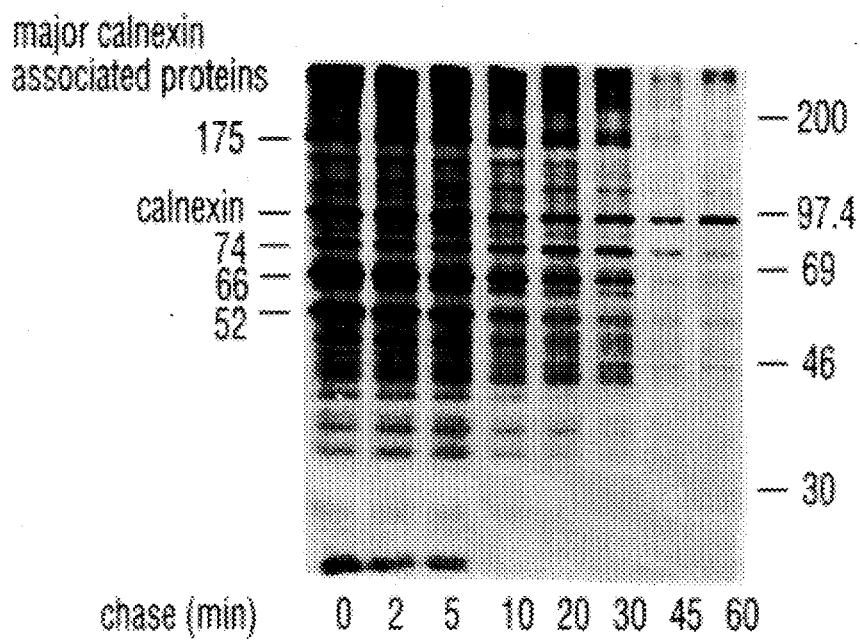
FIG. 3a. HepG2 cells were labeled with 50 μCi/ml Trans $^{35}$S-label for 10 minutes, and chased in DMEM, 1 mM methionine, 0.5 mM cysteine for the indicated times. Cell lysates were immunoprecipitated with anti-calnexin antibody under non-denaturing conditions.
Figure 3C:
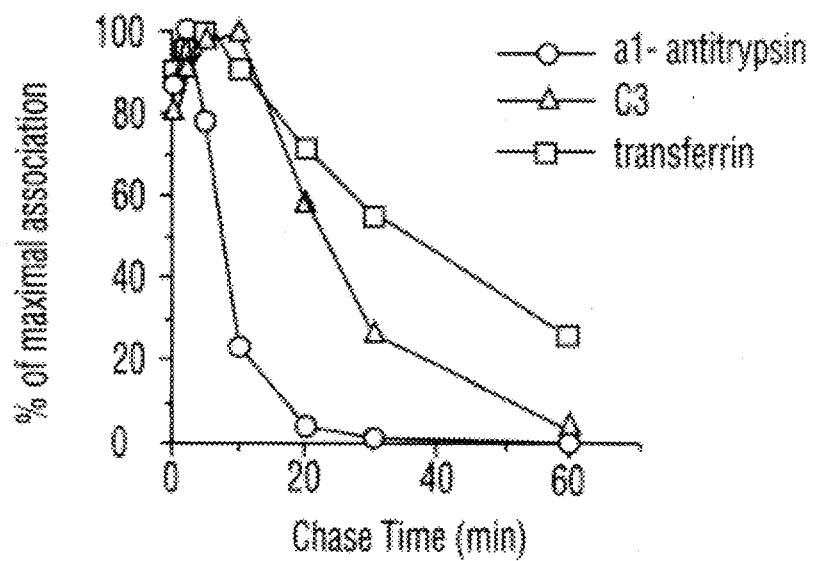
FIG. 3c. Following pulse chase, cell lysates were immunoprecipitated with anti-calnexin antibody under non-denaturing conditions. After elution of the calnexin-associated proteins, sequential immunoprecipitations were carried out with anti-α1-antitrypsin (0-0), anti-transferrin (C—C), anti-C3 antibodies (Δ—Δ). The immunoprecipitates were analyzed by SDS-PAGE followed by fluorography. The intensity of the bands corresponding to the respective proteins were quantitated by densitometry (Zeineh soft laser scanning densitometer interfaced with an IBM PC using GS 350 Data System (Hoefer Scientific Instruments)) and expressed as a percentage of the maximum association found.

Any one of several techniques may be used to detect which secretory proteins are in association with calnexin including those described in detail in Harlow, *Antibodies: A Laboratory Manual*, Cold Spring Harbor Laboratory (1988), incorporated herein by reference. By way of example, suitable methods include immunoprecipitation, followed by peptide mapping and protein sequencing. (FIGS. 1, 2, and 3). Briefly, this entails pulse chasing cells and then immunoprecipitating, employing an anti-calnexin antibody. Anti-calnexin antibodies can be identified using any one of several techniques known in the art, e.g., those described in the Harlow (cited above).

Confirmation of specific interaction may be subsequently accomplished by dissociation of the coimmunoprecipitate with SDS and reprecipitation with secretory protein specific antibody. This technique is described in detail in Harlow, *Antibodies: A Laboratory Manual*, Cold Spring Harbor Laboratory (1988). However, when employing this technique it is important to use the appropriate detergent in precipitation. Suitable detergents include, by way of example, cholate, deoxycholate, digitonin and CHAPS to preserve the interaction, strong detergents, such as Triton X-100 and SDS, tend to destroy the interaction.

Calnexin associations may also be demonstrated or detected by cross-linking with bifunctional agents. This technique is especially for those interested in MHC1 and T cell receptors and is described in detail in Ahluwalia, *J. Biol. Chem.* 267:10914–10918 (1992); Degen, *J. Cell Biol.* 112:1099–1115 (1991); Hochstenbach, *Proc. Natl. Acad Sci. USA* 89:4734–4738 (1992); Galvin, *Proc. Natl. Acad. Sci. USA* 89:8452–8456 (1992).

Calnexin associations may also be demonstrated or detected using in vitro transcription and translation of cDNAs with translocation into microsomal vesicles to experimentally examine associated proteins with the endogenous calnexin present in these vesicles. This technique can be used to easily monitor secretory proteins for their potential to associate with calnexin.

Secretory proteins in transient association (i.e., those which are released after folding) with calnexin include, by way of example, α1-antitrypsin, α1-antichymotrypsin, transferrin, apoβ-100, complement 3 (C3), gp80 human complement-associated protein, and α-fetoprotein.

Secretory proteins retained, i.e., delaying their release into the luminal pathway, by calnexin in the ER include the unassembled T-cell receptor subunits, acetylcholine receptor subunits, HMG CoA reductase, murine class 1 histocompatibility protein (MHC1) (prior to association with β2 microglobulin), and H2a subunit of asialoglycoprotein receptor and any mutant or misfolded glycoproteins. Misfolded or mutant glycoproteins are retained by calnexin and are ultimately degraded by ER resident proteases or transported to lysosomes for degradation.

Suppression of calnexin associations increases the rate of release of secretory proteins. Secretory proteins in transient association with calnexin are translocated through the membrane more quickly. Those which would ordinarily be retained by calnexin are released directly through the luminal pathway.

Calnexin associations can be suppressed using a "calnexin suppressor agent" which, in the context of the present invention, refers to any agent which functions to disrupt or inhibit calnexin associations with secretory proteins using any suitable means including calcium depletion, genetic manipulation, calnexin blocking antibodies, and insertion of antisense sequences. Suitable calnexin suppressor agents for specific secretory problems may be selected by any one of several means, including immobilizing calnexin either by direct lining or by biotinylation and binding to streptavidin to a column and then to use this to interact in vitro with secretory proteins, thereby establishing the binding parameters and any necessary cofactors for the release of proteins. These techniques are described in detail in Harlow, *Antibodies: A Laboratory Manual*, Cold Spring Harbor Laboratory (1988). Alternatively, the changing secretory protein presence due to calnexin associations may be evaluated in the biological preparation by immunoprecipitation of the specific secretory protein before and after the administration of the particular calnexin suppressing agent employed.

In one embodiment of the present invention, the calnexin suppressor agent acts by calcium depletion in the cytoplasm, or more preferably, in the ER. This can be accomplished using any suitable agent including an ionophore, such as valinomycin or nonactin, or a calcium channel blocker, such as verapamil, nifedipine or diltiasem.

In another embodiment of the present invention, calnexin associations are suppressed by administering to the biological preparation or warm-blooded animal a suitable glycosylation inhibitor, including by way of example, tunicamycin, castanospermine, nojirromycin, deoxynojirramycin, or swaisonine.

In another aspect of the present invention, calnexin associations are suppressed by decreasing the temperature of the biological preparation to about 30° C. For example, the retention of CFTRΔF508, which depends on calnexin for folding and translocation, is temperature sensitive. Reducing the temperature of the cell line to 30° C. allows the CFTRΔF508 channel to get to the plasma membrane, presumably by altering the association with calnexin. This technique is described in detail in Pind, *J. Biol. Chem.* 269:12784–12788 (1994).

In another aspect of the present invention, calnexin associations are suppressed by introducing an agonist or antagonist which will competitively inhibit binding of the unfolded secretory proteins. Suitable inhibitors include by way of example, amino acid analogues which incorporate into glycoproteins and produce unfolded proteins under in vivo conditions, such as azetidine-2-carboxylic acid. Calnexin recognizes these analogues, enters into association with them, and then are essentially incapacitated because they are unable to fold and subsequently release them.

In another aspect of the present invention, calnexin suppression is accomplished by treatment of cells with dithiothreitol or diamide to inhibit dissociation of secretory proteins from calnexin. This technique is described in detail in Wada, *J. Biol Chem.* 269(10):7464–72 (1994).

An increase of secretory protein production, and hence the success of the method of calnexin suppressor agent, can be monitored using any one of several techniques, including evaluating the changing secretory protein presence in the biological preparation by immunoprecipitation of the specific secretory protein before and after the administration of the particular calnexin suppressing agent employed. This technique, and other suitable techniques, are described in detail in Harlow, *Antibodies: A Laboratory Manual*, Cold Spring Harbor Laboratory (1988).

Another aspect of the present invention involves a method of treating protein trafficking disorders. Protein trafficking disorders may be treated by suppressing or stimulating calnexin activity depending upon the etiology of the particular disorder.

For example, a warm-blooded animal suffering from a protein trafficking disorder would benefit from the suppression of calnexin activity if the disorder is one in which an otherwise biologically active protein is retained in the ER. Such disorders can be identified by an underproduction of secretory protein recognized by coimmuno-precipitation assays as described in Ou et al., *Nature* 364:771–776 (1993) and include, by way of example, familial hypercholesterolaemia (class 2 mutations in the LDL receptor), cystic fibrosis (CFTRΔF508), Tay-Sachs disease, congenital sucrase isomaltase deficiency, and juvenile pulmonary emphysema.

Secretory proteins which are retained by calnexin within the ER may aggregate therein or be subject to degradation. These proteins may be identified by coimmunoprecipitation assays as described in Ou et al., *Nature* 364:771–776 (1993) and include, by way of example, acetylcholine receptor subunits, HMG CoA reductase, calnexin selectively binds mutant proteins, including, by way of example, α1-antitrypsin, LDL receptors, b-hexosaminidase, CFTR and influenza haemagglutinin and, more specifically, the Z mutation as well as the null Hong Kong mutation of α1-antitrypsin. The interaction of CFTR and the prolonged association of the DF508 mutant protein has been demonstrated and a model is that this association is responsible for the retention of this otherwise functional channel in the ER (Pind, *J. Biol. Chem.* 269: 12784–12788 (1994)).

Calnexin activity can be suppressed by any one of several suitable techniques, including administering a therapeutically effective amount of any one of the calnexin suppressor agents described in detail above. A therapeutically effective amount is determined based on in vitro experiments, followed by in vivo studies.

The calnexin suppressor agents may be administered by injection, infusion, orally, rectally, lingually, or transdermally. Depending on the mode of administration, the compounds or separate components can be formulated with the appropriate diluents and carriers to form of ointments, creams, foams, and solutions.

Injection may be intravenous, intramuscular, intracerebral subcutaneous, or intraperitoneal. For injection or infusion, the compound would be in the form of a solution or suspension. It would be dissolved or suspended in a physiologically compatible solution in a therapeutically effective amount.

For oral administration, the compounds may be in capsule, table, oral suspension, or syrup form. The tablet or capsules would contain a suitable amount to it comply with the general and preferred ratios set forth below. The capsules would be the usual gelatin capsules and would contain, in addition to the three compounds, a small quantity of magnesium stearate or other excipient.

Tablets would contain the a therapeutically effective amount of the compound and a binder, which may be a gelatin solution, a starch paste in water, polyvinyl pyrilidone, polyvinyl alcohol in water or any other suitable binder, with a typical sugar coating.

Syrup would contain a therapeutically effective amount of the compound.

A warm-blooded animal suffering from a protein trafficking disorder which would benefit from calnexin stimulation can be identified by coimmunoprecipitation as described in detail in Ou et al., *Nature* 364:771–776 (1993) and include, by way of example, viral cancers and other viral infections. The assembly of functional viral particles requires viral glycoproteins which are processed through the secretory pathway. This has been confirmed with VSV G protein and influenza HA protein in Hammond et al., *Proc. Natl. Acad. Sci. USA* 91(3):913–7 (1994) and in the case of HIV gp120. The HIV gp120 is slowly translocated through the ER because of its long association with the calnexin. Calnexin stimulating agents may prevent the disassociation of HIV gp120, trapping it in the ER.

In order to suppress the production of the viral particles, calnexin activity is stimulated by the administration of a therapeutically effective amount of a phosphorylating agent. Suitable phosphorylating agents include: casein kinase II, cdc2 kinase, and protein kinase C. A therapeutically effective amount may be determined based on in vitro experiments, followed by in vivo studies.

Depending on the mode of administration, the calnexin stimulating agents can be formulated with the appropriate diluents and carriers to form suitable ointments, creams, foams, and solutions as described above. Methods of administration are the same as those outlined above.

The term "treatment" as used within the context of the present invention, refers to reducing or alleviating symptoms in a subject, preventing symptoms from worsening or progressing, inhibition or elimination of the causative agent, or prevention of the infection or disorder in a subject who is free therefrom. Thus, for example, treatment of infection includes destruction of the infecting agent, inhibition of or interference with its growth or maturation, neutralization of its pathological effects and the like. A disorder is "treated" by partially or wholly remedying the deficiency which causes the deficiency or which makes it more severe. An unbalanced state disorder is "treated" by partially or wholly remedying the imbalance which causes the disorder or which makes it more severe.

Within another aspect of the present invention, methods are provided for delivering vector constructs to a warm-blooded animal or biological preparation, wherein the vector construct directs the expression of calnexin, or calnexin lacking in cytostolic or transmembrane domains, thereby acting as a calnexin suppressor agent or a calnexin stimulating agent.

As utilized within the context of the present invention, "vector construct" refers to an assembly which directs the expression of a gene of interest. The vector construct must include promoter elements, and a sequence which, when transcribed, is operably linked to the gene of interest and acts as a translation initiation sequence. The vector construct may also include a signal which directs poly-adenylation, one or more selectable markers, as well as one or more restriction sites.

Calnexin cDNA may be prepared as the gene of interest by obtaining either in full length or truncated mutants cloned from mammalian cDNA using any one of several methods described in Sambrook et al., *Molecular Cloning: A Laboratory Handbook*, Cold Springs Harbor Press (1989). In the context of the present invention, the gene of interest is composed of a portion of the gene encoding calnexin which, when expressed, would disrupt the normal functioning of calnexin, by way of example. Such a vector may serve to disrupt calnexin associations in both or either of its function of translocation and retention. It functions as a calnexin suppressor agent in any one of several ways, including, by way of example, by introducing vectors containing gene sequences designed to reduce the rate limiting step of association and folding for secretory proteins. Such sequences might include one which is lacking the cytostolic domain. It would as a calnexin stimulating agent by the introduction of vectors which encode additional calnexin sequences, thereby increasing the production and decreasing the rate of secretory protein production.

A wide variety of methods may be utilized in order to deliver vector constructs of the present invention to a warm-blooded animal or biological preparation. For example, within one embodiment of the invention, the vector construct is inserted into a retroviral vector, which may then be administered directly into a warm-blooded animal or biological preparation. Representative examples of suitable retroviral vectors and methods are described in more detail in the following U.S. patents and patent applications, all of which are incorporated by reference herein in their entirety: "DNA constructs for retrovirus packaging cell lines," U.S. Pat. No. 4,871,719; "Recombinant Retroviruses with Amphotropic and Ecoptropic Host Ranges," PCT Publication No. WO 90/02806; and "Retroviral Packaging Cell Lines and Processes of Using Same," PCT Publication No. WO 89/07150.

Vector constructs may also be carded by a wide variety of other viral vectors, including for example, recombinant vaccinia vectors (U.S. Pat. Nos. 4,603,112 and 4,769,330), recombinant pox virus vectors (PCT Publication NO. WO 89/01973), poliovirus (Evans et al., *Nature* 339:385–388, 1989; and Sabin, *J. Biol. Standardization* 1:115–118, 1973); influenza virus (Luytjes et al., *Cell* 59:1107–1113, 1989; McMichael et al., *N. Eng. J. Med* 309:13–17, 1983; and Yap et al., *Nature* 273:238–239, 1978); adenovirus (Berkner, *Biotechniques* 6:616–627, 1988; Rosenfeld et al., *Science* 252:431–434, 1991); adeno-associated virus (Samulski et al., *J. Vir.* 63:3822–3828, 1989; Mendelson et al., *Virol.* 166:154–165, 1988); herpes (Kit, *Adv. Exp. Med. Biol.* 215:219–236, 1989); and HIV (Poznansky, *J. Virol.* 65:532–536, 1991).

In addition, vector constructs may be administered to warm-blooded animals or biological preparations utilizing a variety of physical methods, such as lipofection (Felgner et al., *Proc. Natl. Acad Sci. USA* 84:7413–7417, 1989), direct DNA injection (Acsadi et al., *Nature* 352:815–818, 1991); microprojectile bombardment (Williams et al., *PNAS* 88:2726–2730, 1991); liposomes (Wang et al., *PNAS* 84:7851–7855, 1987); $CaPO_4$ (Dubensky et al., *PNAS* 81:7529–7533, 1984); or DNA ligand (Wu et al., *J. Biol. Chem.* 264:16985–16987, 1989).

A therapeutic amount may be determined by in vitro experimentation followed by in vivo studies.

Yet another aspect of the present invention concerns a method of treating protein trafficking disorders by targeting a suitable calnexin suppressor agent, calnexin stimulating agent, or any other agent designed to monitor calnexin associations and secretory protein production. For the purposes of illustrating this aspect of the invention, "targeting moiety" refers to any polypeptide molecule from a dipeptide up to, and including, any protein or protein containing compound or any functional equivalent, including those without an amino acid basis, that binds to a desired target site. In a preferred embodiment of the present invention, this method is utilized to deliver calcium depletion agents directly to the ER.

Suitable targeting moieties include any moiety which specifically binds to a cell surface receptor preferably an ER membrane receptor and is capable of affecting the protein trafficking pathway. Suitable targeting moieties include proteins, peptides, and non-proteinaceous molecules. Representative examples of suitable targeting moieties include antibody and antibody fragments; peptides such as bombesin, gastrin-releasing peptide, cell adhesion peptides, substance P, neuromedin-B, neuromedin-C and metenkephalin; hormones, including EGF, alpha- and beta-TGF, estradiol, neurotensin, melanocyte stimulating hormone, follicle stimulating hormone, luteinizing hormone, and human growth hormone; proteins corresponding to ligands for known cell surface receptors, including low density lipoproteins, transferrin and insulin; fibrinolytic enzymes; and biological response modifiers, including interleukin, interferon, erythropoietin and colony stimulating factor also constitute targeting moieties of this invention. Moreover, analogs of the above targeting moieties that retain the ability to specifically bind to a cell surface receptor, preferably an ER membrane receptor, are suitable targeting moieties. Essentially any analog having about the same affinity as a target moiety, herein specified, could be used in synthesis of receptor modulators.

In a preferred embodiment, the targeting moiety is an antibody or antibody fragment. Particularly preferred antibodies include monoclonal antibodies having high specificity for an ER membrane receptor and the ability to catalyze the internalization of the conjugate. Suitable antibodies may be selected by assays for internalization known in the art and described in detail in *Cancer Treat. Res.* 68:23, 1993; *Leuk. Lymp.* 9:293, 1993; *Anticancer Drug Des.* 7:427, 1992 (incorporated herein by reference). An anti-calnexin antibody can be produced by methods well known in the art and described in Harlow et al., *Antibodies: A Laboratory Manual*, Cold Spring Harbor Laboratory (1988), incorporated herein by reference. The immunoconjugate comprises at least one agent coupled to an anti-calnexin antibody. A single or multiple molecules of one type of agent may be coupled to an antibody. Alternatively, more than one type of agent may be coupled to an antibody.

The basic requirement of the targeting moiety is that the polypeptide increase the specificity of the therapeutic agent toward the desired site, either in vivo and in vitro, depending on the application. Thus, the targeting polypeptides can include proteins having certain biological activities rendering them specific for desired sites.

Suitable targeting polypeptides include but are not limited to receptors, hormones, lymphokines, growth factors, substrates, particularly compounds binding to surface membrane receptors. Suitable receptors include surface membrane receptors, antibodies, enzymes, naturally occurring receptors, lectins, and the like. Of particular interest are immunoglobulins or their equivalents.

The targeting moiety may be readily labeled or conjugated to a wide variety of molecules, including for example, toxins, fluorescent molecules, magnetic resonance enhancers, and radionuclides. Representative examples of toxins include ricin, abrin, diptheria toxin, cholera toxin, gelonin, pokeweed antiviral protein, tritin, Shigella toxin, and Pseudomonas exotoxin A. Representative examples of fluorescent molecules include fluorescein, phycoerythrin, rodamine, Texas red and luciferase. Representative examples of radionuclides include Cu-64, Ga-67, Ga-68, Zr-89, Ru-97, Tc-99m, Rh-105, Pd-109, In-111, I-123, I-125, I-131, Re-186, Re-188, Au-198, Au-199, Pb-203, At-211, Pb-212 and Bi-212. Methods for labeling or conjugating the targeting moiety to any of the above described compounds or compositions may be readily accomplished by one of ordinary skill in the art given the disclosure provided herein (see also Trichothecene Antibody Conjugate, U.S. Pat. No. 4,744,981; Antibody Conjugate, U.S. Pat. No. 5,106,951; Fluorogenic Materials and Labeling Techniques, U.S. Pat. No. 4,018,884; Metal Radionuclide Labeled Proteins for Diagnosis and Therapy, U.S. Pat. No. 4,897,255; and Metal Radionuclide Chelating Compounds for Improved Chelation Kinetics, U.S. Pat. No. 4,988,496; see also Inman, *Methods in Enzymology*, Vol. 34, *Affinity Techniques, Enzyme Purification: Part B*, Jakoby and Wichek (eds.), Academic Press, New York, P. 30, 1974; see also Wilchek and Bayer, "The Avidin-Biotin Complex in Bioanalytical Applications," *Anal. Biochem.* 171:1–32, 1988).

A calnexin suppressor or stimulating agent may be coupled to, i.e., covalently bonded to, the targeting moiety either directly or via a linker group. It will be evident to those of ordinary skill in the art that a variety of bifunctional reagents may be employed as the linker group. A preferred method is described in U.S. Pat. No. 5,094,848 (the '848 patent), incorporated herein by reference. Briefly, the '848 patent discloses a method of binding a therapeutic agent by a cleavable diphosphate or amidated diphosphate linkage to a protein specific for the targeting site, guiding the therapeutic agent directly to the targeted site. The conjugate so created possesses the ability to selectively deliver one or more agents to the ER.

The conjugate is administered in a therapeutically effective amount in a suitable excipient. The effective amount for a particular conjugate may be determined based on in vitro experiments followed by in vivo studies. Depending on the mode of administration, the complex can be formulated with the appropriate diluents and carriers to form ointments, creams, foams, and solutions. Methods of administration are identical to those outlined above.

In another aspect of the present invention, the a targeting moiety conjugated to a reporting group may be used to detect protein trafficking disorders. By administering a warm-blooded animal or a biological preparation an effective amount of such a conjugate, wherein the agent is a reporter group, such as a radionuclide or magnetic resonance enhancer, and detecting the level of the reporter group, the level of calnexin activity can be ascertained.

The effective amount of conjugate necessary may be determined based upon in vitro experiments, followed by in vivo studies. The step of detecting a radionuclide is typically performed with an imaging camera using a detector appropriate for the particular radionuclides type of emission. These techniques are described in detail in Harlow et al., *Antibodies: A Laboratory Manual*, Cold Spring Harbor Laboratory (1988), incorporated herein by reference. The step of detecting a magnetic resonance imaging enhancer is likewise well known in the art.

By detecting the levels of calnexin in the warm-blooded animals or biological preparation using these well-known techniques and the disclosure herein, those of ordinary skill in the art will be able to gauge calnexin levels and identify protein trafficking disorders or the risk thereof.

The following examples are offered by way of illustration, and not by way of limitation.

EXAMPLES

EXAMPLE 1

Antibody Production

Rabbit antibodies were raised to a synthetic peptide corresponding to the C-terminus of calnexin, i.e., residues 555–573 plus a cysteine residue at the carboxyl terminus (Multiple Peptide Systems, San Diego, Calif.). The peptide was conjugated to keyhole limpet hemacyanin using the cross-linker succinimidyl-4-P-maleimidophenyl butyrate (SMPB) (Pierce). Specific antibodies to the calnexin peptide were purified from the antiserum with peptide-affinity columns. HepG2 cells were preincubated with methionine-free DMEM containing 10% dialyzed FGS for 30 minutes, and then labeled with 50 µCi/ml Tran$^{35}$S-label (ICN) in methionine-free media for 30 minutes. Cells were rinsed twice with cold PBS and once with HBS (50 mM Hepes-NaOH (pH. 7.5), 200 mM NaCl). For non-denaturing immunoprecipitations, cells were lysed in HBS buffer containing 2% sodium cholate, 1 mM PMSF, 5 µg/ml each of aprotinin and leupeptin. Cell lysates were precleared with preimmune serum and Pansorbin (Calbiochem). Affinity purified anti-calnexin was added to the supernatant 2h, (4° C.) followed by protein A-agarose (Calbiochem) and rotated for 1 h at 4° C. Beads were washed three times with HBS containing 0.5% cholate and once with HBS. For immunoprecipitations under denaturing conditions, cells were lysed in HBS containing 1% SGS, lysates were heated in boiling water for 5 minutes and passed 15 times through a 27 gauge needle. After centrifugation, the supernatants were diluted with 10 volumes of HBS containing 1% Triton X-100, and immunoprecipitated with anti-calnexin as described above, except that the HBS washing buffer contained 1% Triton X-100, 0.5% deoxycholate (DOC) and 0.1% SDS. Sequential immunoprecipitations were carried out first under non-denaturing conditions as described above. 0.2 ml HBS containing 1% SDS was then added to the protein A-agarose beads and heated at 90° C. for 3 minutes followed by the addition of 2 ml of HBS containing 1% Triton X-100. After centrifugation, the supernatant was used for a second immunoprecipitation with specific antibodies to proteins secreted by HepG2 cells (Calbiochem) as indicated above. Immunecomplexes were recovered with protein A-agarose, and washed three times with HBS containing Triton X-100, 0.5% DOC, and 0.1 SDS. All immunoprecipitates were analyzed in 7% or 8% SDS-PAGE gels followed by treatment with Enhance (DuPont NEN).

EXAMPLE 2

Association of Secretory Glycoproteins with Calnexin

This example demonstrates the association of secretory glycoproteins with calnexin.

HepG2 cells which have been labeled with Tran$^{35}$S-label for 30 minutes followed by cell lysis and incubation with antibodies to α1-antitrypsin, both the 52 kDa ER form and the 55 kDa Golgi form of α1-antitrypsin were precipitated with only the former being sensitive to endo H (FIG. 1a, lanes 1,2). Quantitations revealed that ca. 50% of the α1-antitrypsin had reached terminal glycosylating compartments of the Golgi apparatus during this labeling period. Immunoprecipitation of cell lysates under denaturing conditions with affinity purified antibodies raised either to residues 555–573 of calnexin (FIG. 1a, lane 3) or residues 487–505 only precipitated calnexin.

However, when immunoprecipitations were carded out with calnexin antibody under non-denaturing conditions, several proteins were coprecipitated (FIG. 1a, lane 4). The major coprecipitated proteins migrated with mobilities of 52 kDa, 66 kDa, 74 kDa, 175 kDa, and ca. 230 kDa (calnexin migrates at 90 kDa). The ER forms of the major secretory glycoproteins of HepG2 cells correspond to similar mobilities, i.e., α1-antitrypsin, 52 kDa; α1-antichymotrypsin, 52 kDa; α-fetoprotein, 66 kDa; transferrin, 74 kDa; C3, 175 kDa; apoβ-100, ca. 230 kDa. This observation predicts that most of the major secretory glycoproteins in HepG2 cells are capable of binding to calnexin. To test this, we designed a sequential immunoprecipitation protocol to identify calnexin associated proteins as described in the legend to FIG. 1.

Following immunoprecipitation with anti-calnexin in the presence of cholate, the calnexin associated proteins (FIG. 1 a, lane 4) were eluted with SDS followed by immunoprecipitation under denaturing conditions with antibodies specific to the respective secretory proteins (FIG. 1a, lanes 5–11). Remarkably, α1-antitrypsin, α1-antichymotrypsin, transferrin, C3 apoβ-100, and α-fetoprotein were found to be coimmunoprecipitated with calnexin. Albumin was not immunoprecipitated from the calnexin eluted proteins (FIG. 1 a, lanes 11) although anti-albumin antibodies clearly precipitated the protein from total cell lysates (lane 12). Quantitation revealed that after 10 minutes of radiolabeling, 25% of newly synthesized α1-antitrypsin, 30% of transferrin and 30% of C3 were coprecipitated with calnexin. As the efficiency of total cellular calnexin immunoprecipitation under these conditions was only 60%, we conclude that at least 50% of each of the newly synthesized secretory glycoproteins were calnexin associated.

However, radiolabeled calnexin was not detected in immunoprecipitates with antibodies to the secretory glycoproteins (see FIG. 1b, lanes 1, 3) because calnexin has a relatively long half-life ($t^{1/2}$ >24 h) and is not efficiently radiolabeled during a short labeling period. Thus, these newly synthesized secretory glycoproteins enter the ER and bind with high efficiency to preexisting calnexin.

EXAMPLE 3

Specificity of Calnexin

The non-glycosylated major secretory protein of HepG2 cells, albumin, was not associated with calnexin, yet the related glycosylated protein α-fetoprotein was, suggesting that only glycoproteins may bind to calnexin. The glycosylation inhibitor tunicamycin was used to evaluate if proteins were selected for association with calnexin because of their N-linked glycosylation. Tunicamycin addition to cells led to the inhibition of glycosylation of α1-antitrypsin and transferrin (FIG. 1b, lanes 1,3 cf. lanes 2,4) and these as well as most other proteins were not coimmunoprecipitated with calnexin (FIG. 1b, cf. lanes 5,6). That only glycoproteins associated with calnexin was also demonstrated by the adsorption of calnexin eluted proteins to Concanavalin-A Sepharose. The major polypeptides associated with calnexin were those which bound to Concanavalin-A Sepharose while calnexin (itself not a glycoprotein) was not bound.

In order to evaluate if newly synthesized glycoproteins were binding with calnexin or formed part of a larger network, the sedimentation properties of calnexin associated glycoproteins were assessed. Sucrose density gradients of lysates of cells labeled for 10 minutes with or without tunicamycin were centrifuged to neat equilibrium. Fractions were collected and immunoprecipitated with anti-calnexin (FIGS. 2a, b), anti-α1-antitrypsin (FIGS. 2c, d) and anti-albumin antibodies (FIGS. 2d, f). The distribution of the radiolabeled calnexin associated proteins was compared to that of calnexin as determined by immunoblot analysis of the fractions (FIGS. 2g, h). In control cells (without tunicamycin), most calnexin (FIG. 2g) is found in fractions 3, 4 which also contain majority of the radiolabeled proteins associated with calnexin (FIG. 2a, lanes 3,4). The highest level of calnexin associated α1-antitrypsin (52 kDa, FIGS. 2a, c) was found in fractions 2, 3 while transferrin (74 kDa, FIG. 2a) was predominantly in fractions 3, 4; C3 (175 kDa) was in fractions 4, 5 and apoβ-100 (≈230 kDa) in fractions 5, 6. Hence, calnexin associated glycoproteins of greater molecular mass separated from those of lower mass as would be expected for individual associations of each glycoprotein with calnexin (there were exceptions; for example, glycoproteins of 28, 30, 35 kDa which we have not identified were found in lanes 3–5 of FIG. 2a) indicating that they form part of a large complex.

The majority of newly synthesized radiolabeled calnexin found in fraction 2 (FIG. 2a) did not correspond to the sedimentation of the majority of calnexin as determined by immunoblot (fraction 3, FIG. 2g) showing that newly synthesized glycoproteins associated with pre-existing calnexin which was not radiolabeled. After tunicamycin treatment most calnexin associations were abolished with the sedimentation of calnexin itself being slightly affected (cf. g, h) now having a distribution close to that of newly synthesized calnexin (b cf. h). The sedimentation of the 52 kDa band which coimmunoprecipitates with calnexin (FIG. 2a) correspond to that of α1-antitrypsin (FIG. 2c) which itself showed an increased sedimentation in sucrose gradients of lysates from tunicamycin treated cells despite a lower mass of the protein (48 kDa, FIG. 2d). By contrast, newly synthesized albumin (unassociated with calnexin) showed similar sedimentation properties whether from control (FIG. 2e) or tunicamycin treated cells (FIG. 2f). Hence, no large network of ER proteins was responsible for the calnexin associations.

EXAMPLE 4

Kinetics of Calnexin Association with Newly Synthesized Glycoproteins as Compared to Endo H Resistance Pulse-chase studies (FIG. 3a) demonstrated the transient association of newly synthesized proteins with calnexin. However, some proteins dissociated from calnexin more quickly than others. By sequential immunoprecipitation (see legend to FIG. 1), the $t^{1/2}$ of α1-antitrypsin association (52 kDa) with calnexin was determined to be 5 minutes (FIG. 2b, lower panel). Transferrin was associated with calnexin with a $t^{1/2}$ of ca. 35 minutes (FIG. 3c), while C3 showed an association with calnexin with a $t^{1/2}$ of 25 minutes (FIG. 3c) as did apoβ-100 ($t^{1/2}$ ca. 25 minutes). For all the proteins tested, maximal binding to calnexin did not appear immediately after the pulse but only after 2–20 minutes of chase. This delay can be explained by the time needed to complete the translation of nascent polypeptide chains (14) with larger proteins (e.g., C3, 175 kDa) requiring a longer time for completion than smaller proteins such as α1-antitrypsin (52 kDa).

Figure 3B:
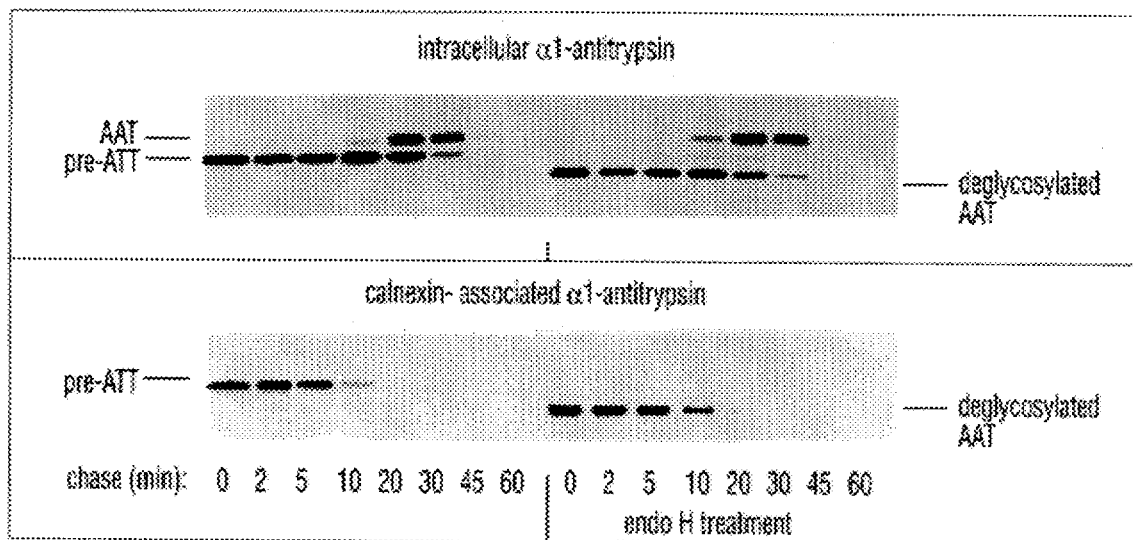
FIG. 3b. Following pulse chase, cell lysates were immunoprecipitated with anti-α1-antitrypsin antibody (upper panel) to determine the kinetics of intracellular transport; (lower panel), after cell lysates were immunoprecipitated with anti-calnexin antibody calnexin-associated proteins were eluted and sequentially immunoprecipitated with anti-α1-antitrypsin antibody as described in length to FIG. 1. The immunoprecipitates were treated with (left) or without (right) endo H at 37° for 15 h.

The acquisition of endo H resistance was used as a measure of the time taken by secretory proteins for ER to Golgi transport. α1-antitrypsin entered Golgi terminal glycosylating compartments as early as 10 minutes with a $t^{1/2}$ of ca. 20 minutes observed (FIG. 3b, upper panel). For C3, a $t^{1/2}$ of 60 minutes was found and for transferrin entry was as early as 30 minutes but the $t^{1/2}$ of acquisition of endo H resistance was extraordinarily long, i.e., >120 minutes. Therefore, there was a differential lag period between the dissociation of these glycoproteins fro calnexin and the acquisition of endo H resistance.

EXAMPLE 5

Association of Misfolded find Incompletely Folded Glycoproteins with Calnexin

Figure 4:
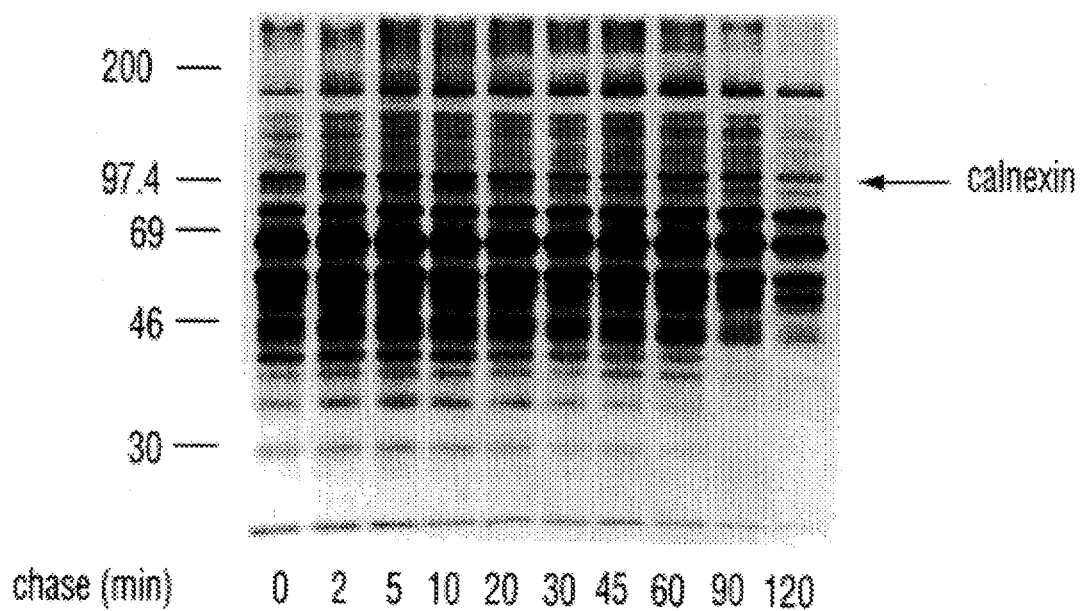
FIG. 4. Time course of the association of newly synthesized proteins with calnexin in the presence of Azc. HepG2 cells were incubated with 5 mM azetidine-2-carboxylic acid (Azc) (Sigma)n in methionine-free medium containing 10% dialyzed FCS for 60 minutes, then pulse labeled with 50 μCi/ml Trans $^{35}$S-label for 10 minutes in the presence of 5 mM Azc and chased in the absence of the drug. At the indicated times, cells were harvested, lysed, and immunoprecipitated with anti-calnexin antibody under non-denaturing conditions as in FIG. 1. Immunoprecipitates were analyzed on an 8% SDS-PAGE gel followed by fluorography. The mobility of albumin would correspond to that of the 69 kDa marker.

The different times of association of glycoproteins with calnexin may be related to their different rates of folding in the ER. Only incompletely folded proteins were tested to determine if calnexin was associated thereto. Two experimental approaches were followed, In the first, the incorporation of the proline analogue, azetidine-2-carboxylic acid (Azc) into proteins was used to interfere with their folding. This has been used previously to demonstrate stable association of proteins with the cytosolic chaperone HSP72 (Beckman et al., Science 248:850–854). In HepG2 cells, pulse labeled in the presence of Azc and chased for various times in the absence of the analogue, newly synthesized proteins remained bound to calnexin (FIG. 4). Albumin in Azc treated cells still did not associate with calnexin. Thus, the association of newly synthesized proteins with calnexin depends on their glycosylation but misfolded glycoproteins once bound are released much more slowly.

Figures 5A, 5B:
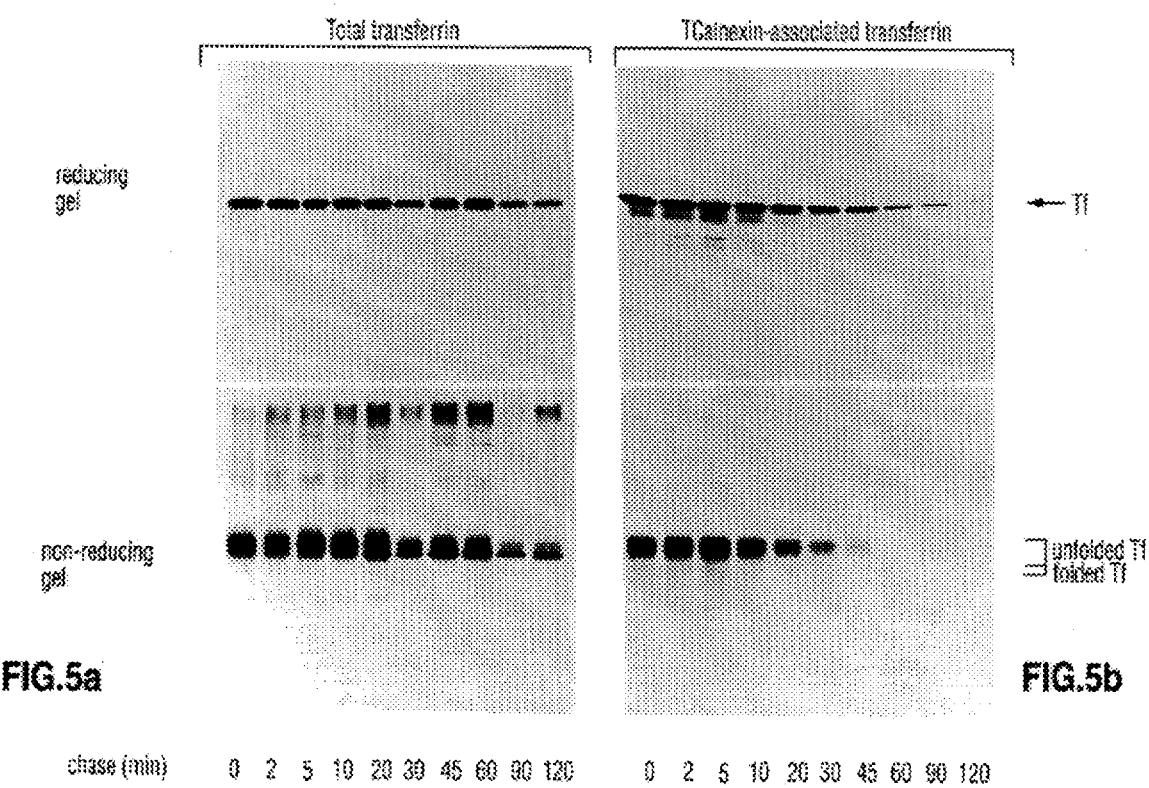
FIG. 5a. HepG2 cells were pulse labeled for 10 minutes with 50 μCi/ml Trans $^{35}$S-label and chased for the indicated times. Transferrin was immunoprecipitated from cell lysates with anti-transferrin antibody, and analyzed on reducing (upper panel) or non-reducing gels (lower panel) as described by Lodish et al. *J. Biol. Chem.* 266:14835-14838 (1991).
FIG. 5b. HepG2 cells were pulse labeled and chased for the indicated times. Total cell lysates were immunoprecipitated with anti-calnexin antibody. Calnexin-associated proteins were eluted from the protein A-agarose beads with SDS and sequentially immunoprecipitated with anti-transferrin antibody as described in the legend to FIG. 1. The higher order aggregates of transferrin are not calnexin associated (cf. a, b, lower panels). They are presumed to represent interchain disulfide bonds and their significance as folding intermediates or misfolded products (Kim et al., *J. Cell Biol.* 118:541–549 (1992)) is unknown.

The second approach directly examined whether calnexin associates only with incompletely folded glycoproteins during normal protein maturation. Lodish and Kong, *J. Biol. Chem.* 266:14835–14838 (1991), have defined conditions to distinguish incompletely folded intermediates during transferrin maturation in the ER of HepG2 cells. They used non-reducing gels to measure the differences in the mobilities of transferrin during disulfide bond rearrangement (there are 19 disulfide bonds in transferrin (Morgan et al., *J. Biol. Chem.* 260:14739–14801 (1985))). After pulse labeling and chase, transferrin immunoprecipitates revealed in reducing gels a sharp band of 74 kDa (FIG. 5a, upper) which was endo H sensitive. On non-reducing gels (FIG. 5a, lower), the major portion of transferrin migrated as a broad, diffuse set of bands at early times of chase (2–20 minutes). This represents the incompletely folded forms of transferrin (c. Gradually, these broad bands were chased to a faster migrating sharper band corresponding to the ER folded form of transferrin with a uniform species of disulfide bonds (Lodish et al., *J. Biol. Chem.* 266:14835–14838 (1991)). Quantitation revealed that ca. 50% of the pulse-labeled transferrin was folded after 30 minutes of chase. The form of transferrin which is in association with calnexin was determined by sequential immunoprecipitation. Transferrin associated with calnexin migrates as a single sharp band on reducing gels (FIG. 5b, upper) but in non-reducing gels (FIG. 5b, lower) only the broad band which represents incompletely folded transferrin is seen. No completely folded transferrin was found in association with calnexin even after 30 minutes of chase. Some aggregates of transferrin were also observed over the time course of the chase (FIG. 1a, lower), but these were not associated with calnexin (FIG. 5b, lower). Hence, calnexin only associates with incompletely folded intermediates of transferrin during maturation but not with aggregated molecules.

From the foregoing it will be evident that although specific embodiments of the invention have been described herein for the purposes of illustration, various modifications may be made without deviating from the spirit and scope of the invention.

We claim:

1. A method of increasing secretory protein production in an ex vivo biological preparation, comprising:

administering a calnexin suppressor agent to a biological preparation in an amount effective to increase secretory protein production.

2. The method of claim 1 wherein said agent acts by depleting calcium.

3. The method of claim 2 wherein said agent is an ionophore.

4. The method of claim 3 wherein said agent is chosen from the group consisting of valinomycin and nonactin.

5. The method of claim 2 wherein said agent is a calcium channel blocker.

6. The method of claim 5 wherein said agent is chosen from the group consisting of verapamil, nifedipine, and diltiasem.

7. The method of claim 1 wherein said agent increases the production of a secretory protein selected from the group consisting of a coagulation factor, a blood factor, a hormone receptor, and an ion channel.

8. The method of claim 1 wherein said agent increases the production of a secretory protein selected from the group consisting of α1-antitrypsin; α1-antichymotrypsin; α-fetoprotein; transferrin; Complement 3 (C3); and apoβ-100.

* * * * *